(12) United States Patent
Trinks et al.

(10) Patent No.: US 6,952,695 B1
(45) Date of Patent: Oct. 4, 2005

(54) SPONTANEOUS ADVERSE EVENTS REPORTING

(75) Inventors: Uwe Trinks, Basking Ridge, NJ (US); Michael Sugerman, Mendham, NJ (US)

(73) Assignee: Global Safety Surveillance, Inc., Little Falls, NJ (US)

( * ) Notice: Subject to any disclaimer, the term of this patent is extended or adjusted under 35 U.S.C. 154(b) by 0 days.

(21) Appl. No.: 09/855,434

(22) Filed: May 15, 2001

(51) Int. Cl.[7] .............................................. G06F 17/30
(52) U.S. Cl. ........................ 707/7; 707/1; 707/101; 707/102; 707/103 R; 707/104.1; 705/3; 705/5
(58) Field of Search ............................ 705/1, 3, 80, 5; 707/1, 2, 3, 4, 5, 10, 101, 102, 104; 709/218; 706/45, 52, 60; 715/513, 530; 600/300, 322, 411, 420, 430, 515

(56) References Cited

U.S. PATENT DOCUMENTS

| | | | | |
|---|---|---|---|---|
| 5,544,044 A | * | 8/1996 | Leatherman | 705/3 |
| 5,601,079 A | * | 2/1997 | Wong et al. | 600/322 |
| 5,924,074 A | * | 7/1999 | Evans | 705/3 |
| 6,128,620 A | * | 10/2000 | Pissanos et al. | 705/3 |
| 6,205,455 B1 | * | 3/2001 | Umen et al. | 715/513 |
| 6,272,370 B1 | * | 8/2001 | Gillies et al. | 600/411 |
| 6,507,829 B1 | * | 1/2003 | Richards et al. | 706/45 |

* cited by examiner

*Primary Examiner*—Shahid Alam
*Assistant Examiner*—Fred Ehichioya
(74) *Attorney, Agent, or Firm*—Goodwin Procter LLP

(57) ABSTRACT

A method of dynamically managing and improving the reliability, accuracy and quality of collected information comprising presenting the user with a hierarchically structured set of predefined terms, receiving reported information from a user corresponding to at least one of the predefined terms, structuring, categorizing and characterizing the reported information, dynamically converting the reported information into a standardized output and storing the standardized output.

32 Claims, 36 Drawing Sheets

HERBS AND NUTRIONAL SUPPLEMENTS

REASONS FOR MEDICATION mydrugsafety.com

HOME | ABOUT US | FIRST-TIME VISITOR | VISITOR BILL OF RIGHTS | PRIVACY POLICY

Welcome to MyDrug Safety

Getting Started

First-time user? Go to our registration page.

You will need some information about your medication. As preparation, please get all your medication bottles, packets and containers.

Our reporting process contains 5 easy steps. At the end, you will receive a summary report for review.

the ⓘ symbol provides online help. If you would like to read all the instructions for all the screens click here to download.

1 Getting Started
Login/Registration instructions
Who are you
Side Effects and/or
Product Complaints userID and Password ⓘ

User ID: _____
Password: _____

Change your Password?

New Password: _____
Repeat Password: _____

[ next ]

*FIG. 5* mydrugsafety.com

HOME | ABOUT US | FIRST-TIME VISITOR | VISITOR BILL OF RIGHTS | PRIVACY POLICY

Patient–Physician Relationship

Getting Started
1 Login/Registration instructions
Who are you
Side Effects and/or
Product Complaints

The Patient/Physician Relationship

To report your information properly, we have to have your physician confirm it. He will not only help you and us to make drugs safer, he can also help you with your side effect. Please provide us with your and your physician's information so that we can call or write back if we need more information. You can do this at any time by clicking on Registration or you will automatically be asked at the end of the process.

There appears to be an incomplete report in progress from the last time you were logged in. Do you want to recover it?

[Clear] [Recover]

*FIG. 6* mydrugsafety.com

HOME | ABOUT US | FIRST-TIME VISITOR | VISITOR BILL OF RIGHTS | PRIVACY POLICY
Instructions

1 Getting Started
Login/Registration
instructions
Who are you
Side Effects and/or
Product Complaints Easy steps to report a Side Effect or Adverse Event STEP 1: Side effect or you are experiencing
STEP 2: Medications you are taking
STEP 3: Reasons for medication
STEP 4: Additional important information
STEP 5: review your report and find out more Easy steps to report a Product Complaint STEP 1: Product complaint
STEP 2: Reason for Medication
STEP 3: Additonal important information
STEP 4: Review your report

[Next]

*FIG. 7* mydrugsafety.com

HOME | ABOUT US | FIRST-TIME VISITOR | VISITOR BILL OF RIGHTS | PRIVACY POLICY

Adverse Event or Product Complaint?    (?)

What Do you Want to Report?

[AE] Adverse Reaction or a Side Effect you are having

[PC] Complaint about your medication

Family Members Data:

Date of Birth [06]–[16]–[70] (mm-dd-yyyy)

or Age [1]

Height [5▼] feet [6▼] inches
(ex: 5 feet 2 inches)

Weight [110] lbs

| Male | Female |

Pregnant ☑ YES

[ next ]

1 Getting Started
Login/Registration
instructions
Who are you
Side Effects and/or
Product Complaints

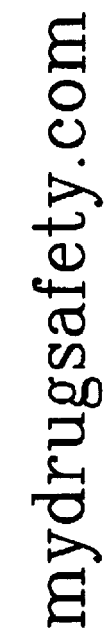
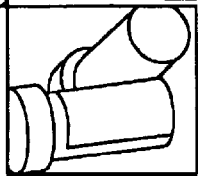
FIG. 10c

General Body

- ☐ Congenital Anomaly
- ☐ Intervention Needed
- ☐ Life-Threatening
- ☐ Died (mm-day-yyyy)
Other ☐

Did it help? ☐ YES
Did something else

Add Symptom to list

Home | About Us | Contact Us | First-time Visitor | Visitor Bill of Rights | Privacy Policy
Copyright 2000 MyDrugSafety.com Limited. All rights reserved.
MyDrugSafety.com is a service provided and managed by global safety surveillance, inc.

Help
{helpscreens}

PatientPort

Home | ABOUT US| FIRST-TIME VISITOR | VISITOR BILL OF RIGHTS | PRIVACY POLICY | Log Out Adverse Event
Lab Results 1. Getting Started
2. Current Side Effects
3. Current Medications
4. Reasons for Medication
5. Additional Important Information
   Patient Information
   Physician Information
   Lab Test Results
6. Review Info & Find Out More

Tell us what tests were done.
Click letter to choose from list.   ABCDEFGHIJKLMNOPQRSTUVWXYZ   (?)

Then Select the appropriate test and method for the specimen. enter results. Standard values for the test will be presented with an indicator for whether the patient values are within range or out of range.

| Test | Specimen | Method | Min-Max | test Value Measurement Time & Date | Status of Test |
|------|----------|--------|---------|-------------------------------------|----------------|
| Abumin | Serum | Colimentry | 3.5–5.0 g/dl | [   ] [g/dl▼] [time▼]<br>[dd▼] [mmm▼] [year▼]<br>○ Multiple test values at this date? | ○ |
| Aldolase | | | | [   ] [g/dl▼] [time▼]<br>[dd▼] [mmm▼] [year▼]<br>○ Multiple test values at this date? | ○ |
| Aldosterone | | | | [   ] [g/dl▼] [time▼]<br>[dd▼] [mmm▼] [year▼]<br>○ Multiple test values at this date? | △ |
| Alkaline | | | | [   ] [g/dl▼] [time▼]<br>[dd▼] [mmm▼] [year▼]<br>○ Multiple test values at this date? | △ |
| Phosphatase | | | | [   ] [g/dl▼] [time▼]<br>[dd▼] [mmm▼] [year▼]<br>○ Multiple test values at this date? | ○ |

[Next]

*FIG. 14b* mydrugsafety.com

HOME | ABOUT US | FIRST-TIME VISITOR | VISITOR BILL OF RIGHTS | PRIVACY POLICY

Adverse Event Product Complaint
Check your record this Report

A ~30year old pregnant 1 patient, weighing 110 pounds, height 5 feet 6 inches, was taking lamisil 1% CREAM 4 Times a day since 07-01-2000, since [how long] [or continuing], for [indication/condition], reportedly experienced an event ['verbatim or reported' term/symptom (R/L/B)] on [date]. This report was received by [pharmaceutical company or GSS] on [date] from [reporter name].

The patient was also taking [prescription medication, over-the-counter or nutriceutical products: concomitant drug 1 (dose, formulation, number of times/day, how long or continuing) for (indication/condition); concomitant drug 2 (dose, formulation, number of times/day, how long Anything to add?

Blablablabla

[Previous] [Next]

1. Getting Started
2. Current Side Effects
3. Current Medications
4. Reasons for Medication
5. Additional Important Information
6. Review Info & Find Out More Review narrative
Review Your Info
Other Simular Reports to the FDA Help Home | About Us | Contact Us | First-time Visitor | Visitor Bill of Rights | Privacy Policy
Copyright 2000 MyDrugSafety.com Limited. All rights reserved.
MyDrugSafety.com is a service provided and managed by global safety surveillance, inc.

*FIG. 15* mydrugsafety.com

HOME | ABOUT US | FIRST-TIME VISITOR | VISITOR BILL OF RIGHTS | PRIVACY POLICY
Review Your & Who Record
Summary Report
pat1 patlast Report is complete Review and Edit your report, Type over text to edit and only when complete press
A. Patient Information Patient Name: pat1 patlast
Date of Birth: 06-16-70
Age at Event: -30
Gender: ○Male ○Female
Pregnant?: ●Yes ○No ○Unknown
Weight: 110 Lbs
Height: 5 ▼ feet 6 ▼ inches
(ex: 5 feet 2 inches)

A. Adverse Event
Results

☐ Died On _____ (mm-day-yyyy)
☐ Hospitalized Less than 24 Hrs
☐ Hospitalized over 24 Hrs
☒ Disability
☐ Congenital Anomaly
☐ Intervention needed
☐ Life threatening
☐ Other Date of Event: _____ (mm-dd-yyyy)
Date of Report: 01-23-2001 (mm-dd-yyyy)

1 Getting Started
2 Current Side Effects
3 Current Medications
4 Reasons for Medication
5 Additional Important Information
6 Review Info & Find Out More
  Review narrative
  Review Your Info
  Other Similar Reports
  to the FDA

FIG. 16a

Description

Event Abated? ○Yes ○No ○Unknown
Event Reappeared? ○Yes ○No ○Unknown

C. Suspect Medications
Drug Name          Dose    Therapy Dates/Duration              Reason
Lamisil            1%      From 07-01-2000 to 01-01-2001 Duration:1    Disease 2

D. Concomitant Medication
Drug Name          Dose    Therapy Dates/Duration              Reason Previous  Next Home | About Us | Contact Us | First-time Visitor | Visitor Bill of Rights | Privacy Policy
Copyright 2000 MyDrugSafety.com Limited. All rights reserved.
MyDrugSafety.com is a service provided and managed by global safety surveillance, inc.

Help

{helpscreens}

FIG. 16b

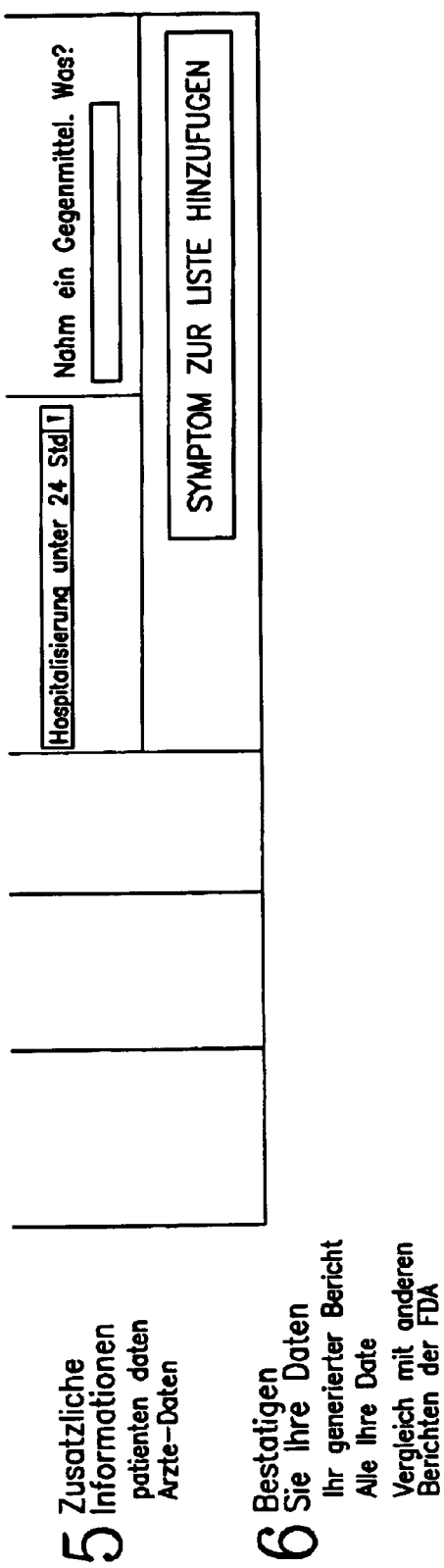

SPONTANEOUS ADVERSE EVENTS REPORTING

BACKGROUND OF THE INVENTION

National health authorities and governmental regulatory Agencies in major countries require Pharmaceutical Manufacturers to collect and report Adverse Drug Reactions, Adverse Events, Product Complaints and Device Failure Complaints, and to provide Full Disclosure about the side effects, risks and contraindications associated with their products. Reports of Adverse Events are received by pharmaceutical manufacturers via letter, fax, e-mail or telephone and are usually processed by safety professionals. The process consists of a series of sequential and/or concurrent sub-processes: Intake, Investigation and Follow-up, Analysis and Reporting. The Adverse Event is usually received as a report (Narrative Verbatim) and is then processed by a healthcare professional, entered into a database system, catalogued and linked to a dictionary of international standard medical terminology such as the terms found in MedDRA, the Medical and Drug Regulatory Affairs Code, or other nationally or internationally recognized coding schema such as World Health Organization's Adverse Reactions Terminology (WHO-ART) Dictionary, or the U.S. Food and Drug Administration's (FDA) Coding Symbols for Thesaurus of Adverse Reaction Terms (COSTART) schema, either by hand or assisted by a semi-automated processes, called auto-encoding.

The investigation and follow-up sub-processes aim at having the event verified and validated by a healthcare professional (physician, hospital). A judgment is reached, whether the Adverse Event report is serious (according to existing definitions established by a national health authority or drug regulatory agency) and unknown, (unlabeled) in which case a report has to be filed with the health authorities within a short period (usually 15 days). All other cases are regularly analyzed and reported on an annual or semi-annual basis in accordance with the laws, regulations or guidelines set forth by a national health authority or drug regulatory agency.

In cases where the Adverse Event occurred in a foreign country or was received by a license taker of the manufacturer, the reports are transferred between manufacturer's safety organizations, requiring rapid information transfer and rigorous quality assurance measures. Special measures have to be taken in cases where reports or data get translated from one language to another. The aim of the reporting process is to discover previously unknown Adverse Drug Reactions, Drug-Drug Interactions, Drug-Food Interactions or other safety issues at an early stage.

The use of standardized terminology is intended to bring uniformity to the reporting for a large international user base with varied linguistic and cultural differences in reporting Adverse Events and Product Complaints. It is intended as a pragmatic, clinically validated compendium of medical terminology with an emphasis on ease-of-use of data entry, retrieval, analysis and display, with a suitable balance between sensitivity and specificity, within the regulatory environment. A standardized dictionary, such as for example MedDRA is applicable to all phases of development for a drug product and the period during which a drug product is sold, and is also applicable to the product life cycle of most medical devices. By providing one standard of medical terminology, the effectiveness and transparency of medical product regulation worldwide is improved. Standardized terminology for reporting Adverse Events or Product Complaints is grouped in three main associations:

Equivalence: synonymous terms are grouped together.

Hierarchical: provides vertical links between superordinate (broad grouping terms) and subordinate descriptors Associative: allows terms, which are neither equivalent nor hierarchically related but may be related by sign, symptom, body system or organ class, disease and/or diagnosis to be linked horizontally (Special Search Categories).

A standardized dictionary can contain many terms. For example, in the current version of MedDRA at each level is has approximately the following number of terms:

a System Organ Class (SOC)—26

High Level Group Term (HLGT)—334

High Level Term (HLT)—1,663

Preferred Term (PT)—approximately 11,000; International Level of Communication

Lowest Level Term (LLT)—approximately 46,000; Synonyms

The use of multiple standardized terminologies however in reporting and codifying Adverse Events poses challenges and creates coding requirements with respect to accurately assessing information collected vis-à-vis a single Adverse Drug Reaction or Adverse Event case, or trending information collected across multiple cases albeit for a single drug product or even for similar but not identical drug products that produce the same desired therapeutic effect through similar mechanisms of action within the human body. Because of the large number of terms, there are sometimes too many choices to describe a particular Adverse Event or device complaint. In addition, there are problems due to the fact that each reported event requires a written verbatim narrative of the event, which requires that the safety professional be well versed in the standardized formats and terminologies employed to catalog and characterize various Adverse Events and Product Complaints. Selection of the proper term and creating a highly standardized and structured format applied to each verbatim report are difficult and time-consuming processes requiring great care.

What is desired therefore is a system and method for assisting and rigorously structuring in the intake, investigation and Follow-up, Analysis and Reporting of all Adverse Events and Product Complaints, but especially spontaneously reported cases.

It is also desired to provide a system and method for standardizing Adverse Event and Product Complaint reporting. In that way an untrained health professional or a company employee assigned to receive, process and record. Adverse Event reports or can receive and record event reports without the need for intensive training in safety, safety data and information collection, applying and utilizing various coding schema, or applying and utilizing requisite clinical safety knowledge. In addition, with such a system, a patient can, in a highly effective, efficient and standardized manner, report meaningful safety data and information directly to an interested party such as his/her treating physician or a manufacturer of a drug product.

It is also desired to provide a system and method to efficiently generate Adverse Event and Product Complaint reports in order to comply with event reporting time deadlines.

It is also desired to provide a system and method to efficiently, safely and seamlessly transfer the collected data into any standard industry drug safety system, using industry standard protocols and definitions like the E2B and E2C standards defined by the International Conference on Harmonization of Technical Requirements for Registration of Pharmaceuticals for Human Use. (ICH M1-3).

It is also desired to provide a system and method to collect and manage data utilizing a network computer system operating in a stateless environment, while having the ability to maintain and manage state.

SUMMARY OF THE INVENTION

The present invention overcomes the drawbacks of the prior art by providing in a first aspect a method of dynamically managing and structuring the input and improving the reliability, accuracy and quality of collected information by presenting the user with a hierarchically structured set of predefined terms, receiving reported information from a user corresponding to at least one of the predefined terms, categorizing and characterizing the reported information, dynamically converting the reported information into a standardized output and storing the standardized output.

BRIEF DESCRIPTION OF THE DRAWINGS

These and other objects and advantages of the invention will become more apparent from the following detailed description of a preferred embodiment of the invention when taken into conjunction with the drawings wherein:

FIG. 3i is a flow chart depicting, a detailed, exemplary site flow diagram for the present invention.

FIG. 5 is a depiction of an exemplary version of a user login page for the interface of the current invention.

FIG. 6 depicts an exemplary physician patient consent page.

FIG. 7 depicts an exemplary instructions page for the interface of the present invention.

FIG. 9 is a depiction of an exemplary report designation page.

FIG. 10b is a depiction of an exemplary Adverse Event reporting page.

FIG. 10c is a depiction of an exemplary Adverse Event reporting page.

FIG. 10d is a depiction of an exemplary non-English language Adverse Event reporting page.

FIG. 11 is a depiction of an exemplary medication reporting page.

FIG. 14 is a depiction of an exemplary medical condition-reporting page.

FIG. 15 is a depiction of an exemplary written narrative report.

DETAILED DESCRIPTION OF THE PREFFERED EMBODIMENT

Figure 1:
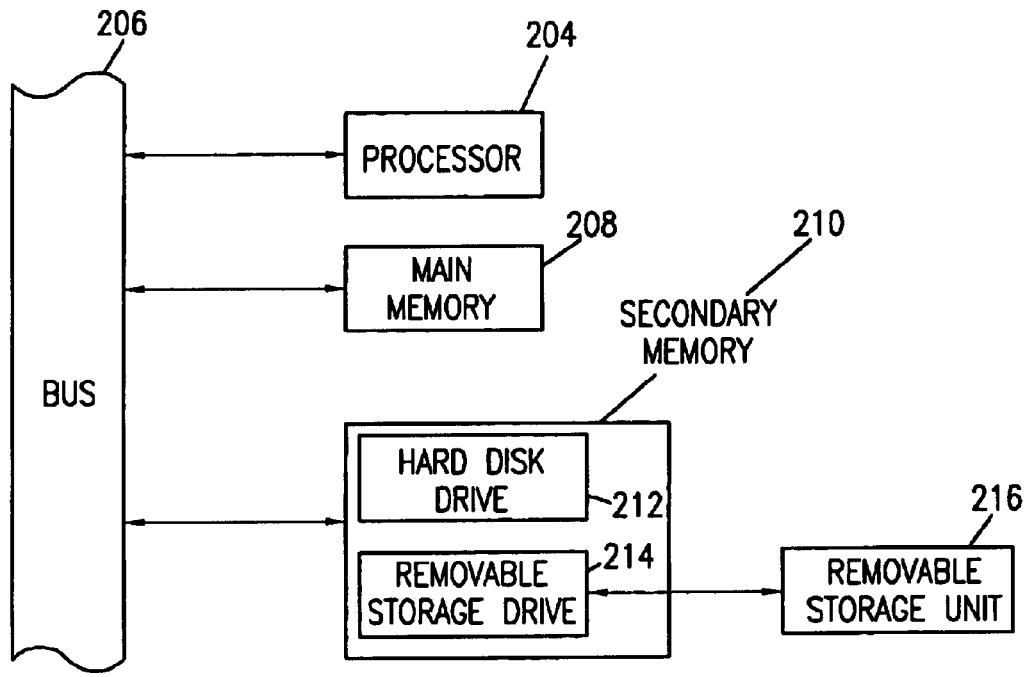
FIG. 1 is an exemplary computer system for implementing the present invention.

TABLE OF CONTENTS
I. Introduction
II. User Interface
III. Database Terminology Standardization
IV. Database Encoding
V. Embodiments I. Introduction The present invention will now be described in detail with reference to the accompanying drawings. While the present invention is described in the context of an Internet based communications network, which includes a specific number and type of components, the system of the present invention may be incorporated into data and voice communications networks of many structures and sizes. The drawings are intended to provide one example of a communication network configuration in which a system of the present invention may be implemented and are not intended to limit the applicability of the present invention to other network configurations. For example, all of the features of the present invention could be implemented using a voice recognition system, wherein the user could access the system via a landline or wireless mobile communications device and enter information via responses to auditory choices and menus, or to text prompts on a wireless pager.

As will be disclosed below, an aspect of a preferred embodiment involves a process for entering, accessing and encoding data, in any language, through a super-secure portal for Spontaneous Adverse Events Reporting, Medical Product and Device Complaint Reporting Medical Inquiries and registry functions. The Portal is accessed from a Web-Browser via the WWW using strong encryption and HTTPS as the sole protocol between browser and application. No active content is needed in the browser to run the application.

With reference to the various systems and methodologies of the present invention, as described below, aspects of the present invention are described in terms of steps, some of which being executed or executable on a computer system. Various implementations of the inventive systems and methodologies provide a comprehensive, multifaceted; multi-user based incident reporting system and method. In accordance with these implementations, there is provided a system and method for entering, accessing and encoding data through a super-secure portal for Spontaneous Adverse Events Reporting, Medical Product and Device Complaint Reporting and Medical Inquiries. In other aspects of the invention, which are discussed in much more detail below, the data encoding routine of the present invention presents a novel method to populate the database in order to provide high accuracy and data entry redundancy.

In a preferred implementation, a central database is developed and contains information pertaining to Adverse Events Reporting, Medical Product and Device Complaint Reporting and Medical Inquiries and individual patient information, which preferably is incorporated into the database corresponding to each reported event or complaint. Other types of information can be incorporated, as will become apparent below. Preferably the data fields are named in accordance with the E2B and E2C standards issued by the international committee for harmonization (ICH M1-3).

Through the use of the present invention, the process of developing the database incorporates techniques to ensure that the information reported is reliable and accurate. Accordingly, redundant data input systems and methods are incorporated to ensure the reliability and accuracy of reported information through the various systems and methodologies of the invention. Information concerning the patients' condition, prescribed medication, Adverse Events and complaints are entered into the database through a user interface wherein the user selects information to be included in the database using pull down menus. In addition, once the data is selected, the user must confirm the reported information at least twice. Thus through the immediate review and detection of data input errors, corrective action can be undertaken immediately, by the incident user, therefore increasing the reliability and accuracy of the reported information.

In accordance with one aspect of the invention, patient information, medication information, Adverse Event and Product Complaints are received from the user via the input interface. Data is input through the interface-using either pull down menus or free form data entry fields. The pull down menus include a set of clickable data entries for each data categories. In the event that user is unable to locate the data entry from the provided pull down menus that accurately reflects the patients information or condition, then the user can enter that information in a data entry field. However, any data that is entered via the data entry field rather than chosen from a pull down menu is automatically flagged for verification and validation.

In accordance with one aspect of the invention, patient information is provided and can be accessed by a user or safety monitor through an exclusive password-protected system. In this way, a flexible and paperless reporting environment meets the demands of real-time secure and reliable information needs of patients, treating physicians, clinical investigators and safety monitors within product manufacturers and their licensees and partners. In other aspects, safety reports can be generated from the event reports for use in reporting significant events, or in transferring case reports to another database or data repository.

Computer System Overview

Although a variety of different computer systems can be used with the present invention, an exemplary computer system is shown generally in FIG. 1.

Computer system includes a host computer having a processor 204, main memory 208, a secondary memory 210 comprising a hard disk drive 212 and a removable storage drive 214. The exemplary components of host computer are operably connected via an address/data bus 206, which is not specifically designated. Memory can, and preferably does include a volatile memory (e.g. random access memory) which is coupled with the data bus for storing information and instructions for processor, and a non-volatile memory (e.g. read only memory) coupled with the data bus for storing static information and instructions for processor. Data storage device can comprise a mass storage device. Host computer constitutes a hardware platform, which executes instructions to implement the application mil program(s) described below. It will be-understood that system, as set forth in FIG. 1, is a schematic representation only. Accordingly, the system as described above and below can be implemented as an integral stand alone system as suggested by FIG. 1, or can include separate component parts which are interconnected and operable for implementing the invention described below.

Interface device preferably comprises a multi-user network interface (e.g. an Internet interface), which couples computer system to a multi-user system (e.g. the Internet in one embodiment of the present invention). Interface is coupled to permit communication with various application programs contained on the hardware platform defined by computer system. The Interface can typically be implemented using a graphical user interface (GUI) incorporating pull down menus and data entry fields.

As mentioned above, and in a preferred implementation of the present invention, interface device comprises an Internet interface. The Internet is a well-known connection of worldwide computer systems that operate using a well-known Internet protocol. The Internet is one type of multi-user computer system. Other Internet applications (e.g. using specific protocols) operate on top of the Internet protocol. One such application is the well-known World Wide Web or "www" Internet application that operates using the hypertext transfer protocol or http. The "www" Internet application is a "demand system" in which user requests information from a site and the site transfers the information back to the user on-line. Also well known is the email Internet application which operates using the simple mail transport protocol or SMTP. The email Internet application is a "present system" in that an information transfer command originates from a sender site and information pursuant to that command is presented to the target email address. Another Internet application is the file transfer Internet application that operates using the file transfer protocol ftp. In one embodiment, the present invention utilizes the www, email, and file transfer Internet applications as well as the Internet protocol. Other embodiments of the present invention can be implemented in other multi-user computer environments. For example, the present invention could be implemented with a dedicated multi-user system.

Computer system supports a software configuration, which operates under control of a conventional operating system. The operating system permits various application processes to be executed. These include, for example, a communications application that permits data transfer with various remote terminals as will become apparent below. The software environment further includes a data management, storage, and retrieval application that is utilized in connection with data storage device. The data management, storage, and retrieval application organizes and stores information, which will be described in greater detail below. This information is organized and stored within the environment of the operating system on one or more mass storage devices such as data storage device. Other applications conventionally known may be included in the software environment comprising computer system.

Figure 2:
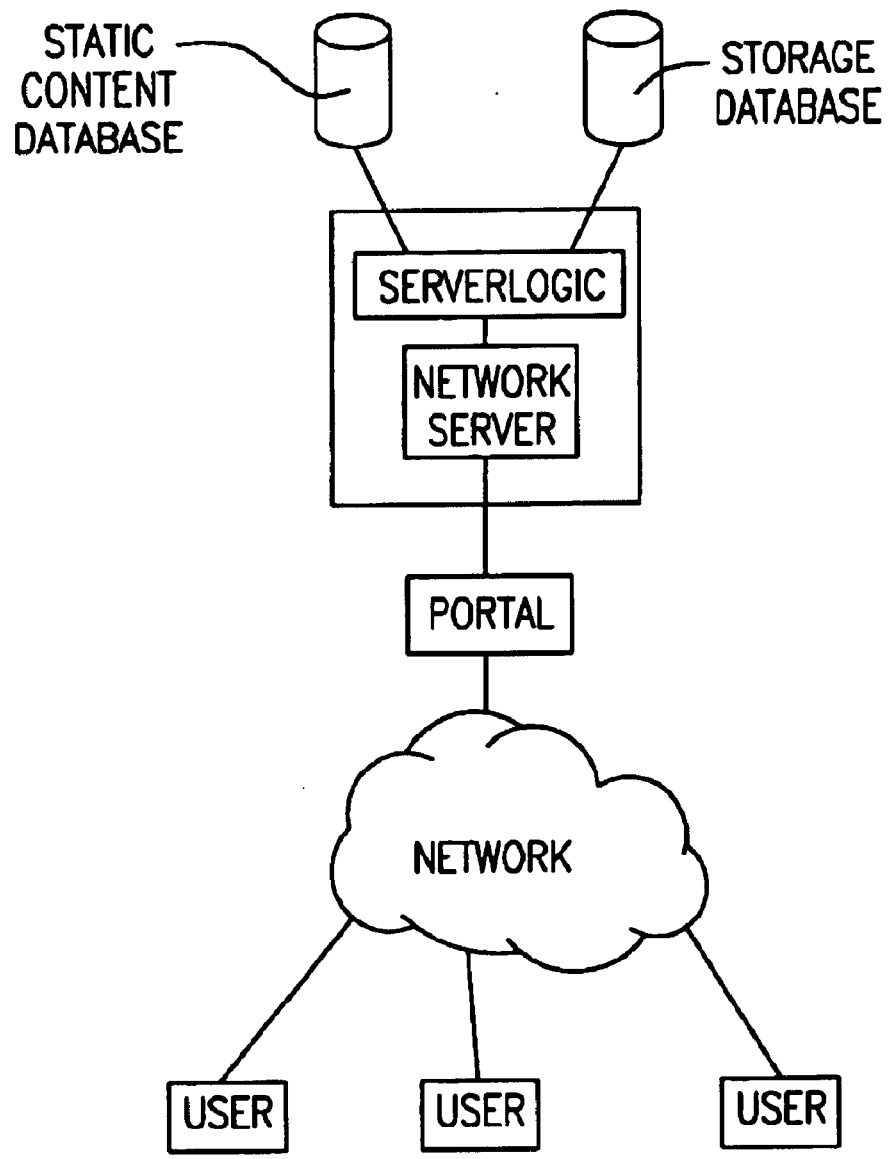
FIG. 2 is an exemplary computer network system for implementing the present invention.

In view of the foregoing computer system description and in accordance with one aspect of the invention, the reader is referred to FIG. 2. There, an exemplary computer system or host system can be seen to comprise part of a network, which includes a database host, a network and a user. In the context of this document, the term "database host" will be understood to include a secure portal hosting the computer program that embodies the current invention, a network server controlled by the server logic (software) and a database for storing site content and input data. The network. Similarly, the term "user" as used in this document will be understood to include a patient, event user, a physician or safety monitor.

The present invention can be implemented with a software program executable on computer system. Such program would typically be stored in memory. A plurality of, dictionaries and thesauri are defined in host computer database. Such dictionary and thesauri are stored within a database that is preferably stored within a storage device, such as data storage device. The user interface, as described below includes a plurality of pull down menus. Each pull down menu contains a list of popular terms used to describe a symptom, medication or indication. The terms contained in the pull down menus are stored in a dictionary and/or thesaurus and are written to the interface display by the software of the present invention. Each of the popular terms on the user interface is hard coded to a corresponding standardized term. The thesaurus contains information associated with each data entry field of the user interface. Each pull down menu or data entry field that is incorporated into the GUI will be associated with a particular data field in the thesauri. Each data field in the thesauri, corresponding to a user data entry field is also associated with a particular standardized term or code from a standard medical dictionary, such as MedDRA, ICD-9, or WHOART. A data entry contained on the pull down menus is hard coded to at least one field in the thesauri containing a standardized term for that selection. The standardized term, such as from MedDRA, is in turn populated into the database for a particular reported event. In that way it is possible to ensure that the appropriate term is encoded for all entered data. The reported information can include any type of information that is useful in implementing the present invention. Exemplary information includes the user's ID and password, the users reporting status, for example patient, family member, or treating physician, patient information such as age, height and weight, prescribed medication, and categorizations, characterizations and descriptions of an Adverse Event or Product Complaint. Additionally, particular information regarding the Adverse Event can be included. Exemplary Adverse Event information can include, such things as Body Region; Head: Sub Region; Eyes: Symptom; Blurred Vision: Preferred Term; Vision blurred, and various other information as well.

Adverse Event or Product Complaint information is transmitted from a user to a host computer. The Adverse Event or Product Complaint information pertains to at least one event or complaint experienced by the customer. The Adverse Event or Product Complaint information can be introduced into system in any suitable way. In a preferred embodiment, such information from a user is received electronically, via a suitable data link with host computer, using one or more of the Internet protocols mentioned above. Other methods and systems can, of course, be utilized to permit such information to be received by host computer.

In a preferred implementation, the information that is received into the host computer for each patient pertains to a plurality of different Adverse Events, Product Complaints, medications and symptoms.

The interface of the present invention is described as being presented to the user through the graphical user interface of an Internet browser program. The browser's graphical user interface (e.g., Netscape™ Navigator™) presents content provided by a resource (e.g., a file) at a URL (Universal Resource Locator). The content can include graphics, text, animation, sound, instructions, etc. A URL can refer to a location on a remote computer that stores the content as data and presentation instruction. The presentation instructions and data can be in a variety of formats such as HTML (Hypertext Markup Language), XML (Extensible Markup Language), PDF (Portable Document Format), JPEG (Joint Photographic Experts Group), and MPEG (Moving Picture Experts Group). When browser requests content from a URL resource, a remote computer providing the resource can transmit the content to a browser for presentation. As shown, the browser is an independent application, however, other applications (e.g., an e-mail program, a work processor, or a spread-sheet) can incorporate functions traditionally performed by the browser.

II. User Interface

The Graphical User Interface guides the user through the application through a standardized flow. In the present invention, the user interface is designed so that once the user inputs required information, successive step are presented automatically. Furthermore, structuring and; standardization of input information are achieved by providing the user with pull down menus for data entry. Free form data entry fields are provided as a backup for the pull down menus. While the interface of the present invention is described as displayed in a web browser window, this description is exemplary of one preferred embodiment of the present invention, those skilled in the art will recognize that many other embodiments with other types of interface elements may be used to provide the same or similar functionality as web browser window.

FIGS. 3–16 illustrate the data collection and reporting aspects in one embodiment of the present invention. One skilled in the art would appreciate that these various web pages as well as the data fields and links displayed on each page can be omitted, amended, rearranged or adapted in various ways. Furthermore each page may contain cross-referenced links to other pages within the site. In that way the user can directly access a particular page as needed.

Figure 3:
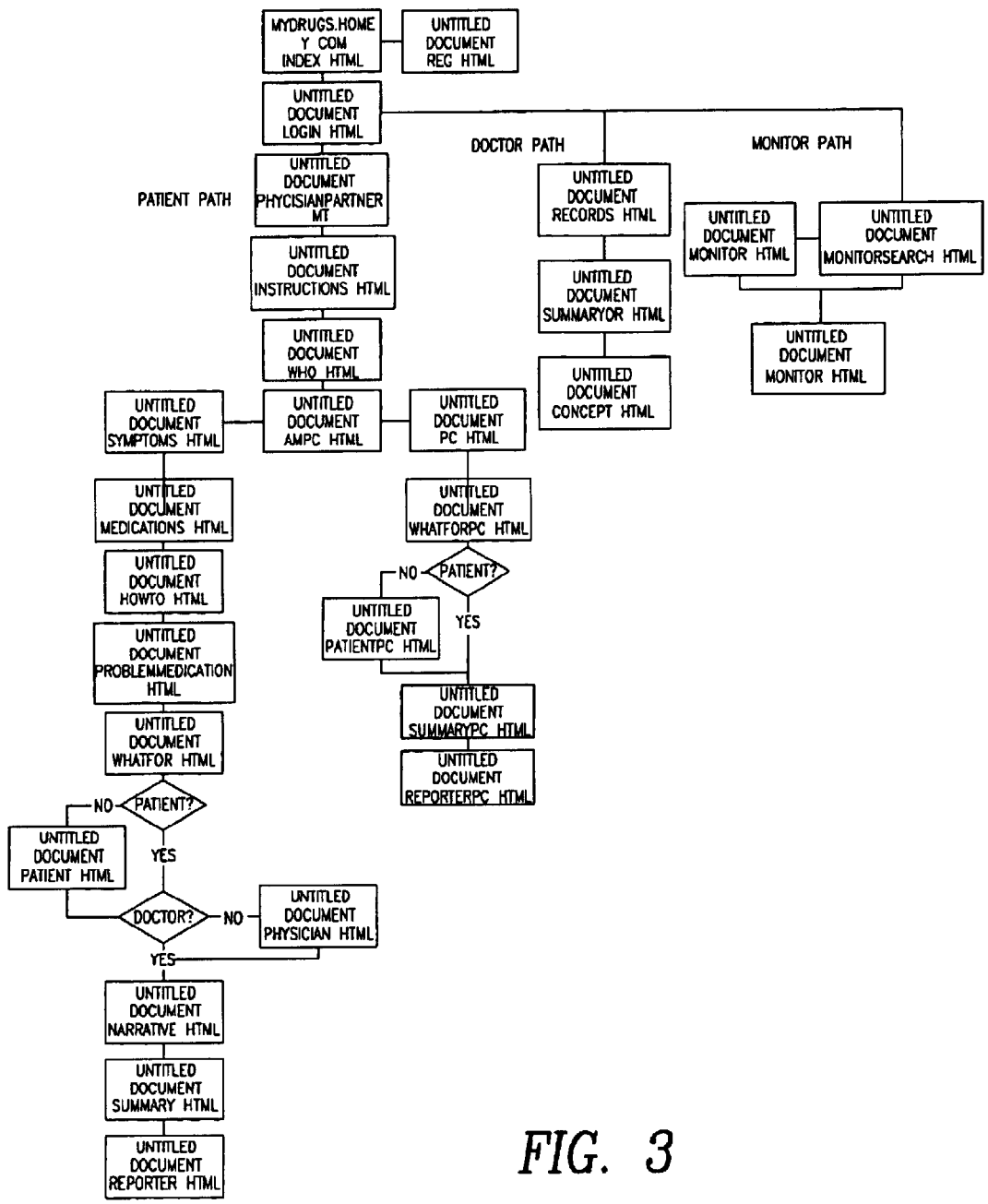
FIG. 3 is a flow chart depicting an exemplary site flow diagram for the present invention.

Turning now to FIG. 3, there is shown a flow chart depicting an exemplary site flow diagram for the present invention. The user upon accessing the site is presented with an index of the site. This includes; the Patient reporting path, the Physician reporting path and the Monitor reporting path. The index page also contains a link to the registration page for first time users. The user is first presented with a page displaying a site index. The site index page displays information regarding the various reporting section of the interface along with a text, representing a link to each section of the site embodying the present invention This example Web page was sent from the server system to the client system.

This example Web page contains a free form field for entry of users UserID and Password as well as fields to change a users password. In addition there is a link to the registration page for first time users to input registration information. On the Instructions Page, there is included a step-by-step instruction for reporting either; a Side Effect or Adverse Event, or a Product Complaint. The user is directed from the login screen to the patient path, the physician path or the monitor path.

Within the patient path the user is presented with a login screen, a physician patient consent screen, instructions for entering the event report, a screen for the user to indicate his or her identity and a page to initiate either a Adverse Event report or a Product Complaint. To report an Adverse Event the user is presented with a succession of pages to input information regarding symptoms, medication being taken and herbs and nutritional supplements being taken. The user is then requested to identify the medication or supplement that is suspected of having caused the Adverse Event and the reason that the medication or supplement was taken by the patient. It would be obvious to one skilled in the art to modify these text selections choices to be represented as pictures of medications and supplements. If the user is the patient, the user is requested to supply information regarding the identity of his or her physician. Likewise, if the user is a physician, the user is requested to supply information regarding the identity of the patient experiencing the Adverse Event.

Upon completion of the data entry, the user is presented with a written narrative and a summary report in order that the user can confirm the information entered. Finally the user is asked to confirm his or her identity.

The Product Complaint path is similar to the Adverse Event path, with the obvious difference being that the user reports information regarding a Product Complaint.

The physician path provides an interface for a physician to access reports made by or about a patient. By utilizing this feature of the present invention, a physician will be able to review reports made by a patient to correct errors or enter additional information. To use this feature, a physician will, using a password access a list of reports made by or for his or her patients. The list will provide links to the full event reports that the physician can review to either correct or confirm.

Finally, there is provided a monitor path wherein a safety monitor can review all reports for further follow-up as needed. The monitor can view a list of reported cases, which can be indexed and accessed according to well-known principles.

Figure 3A:
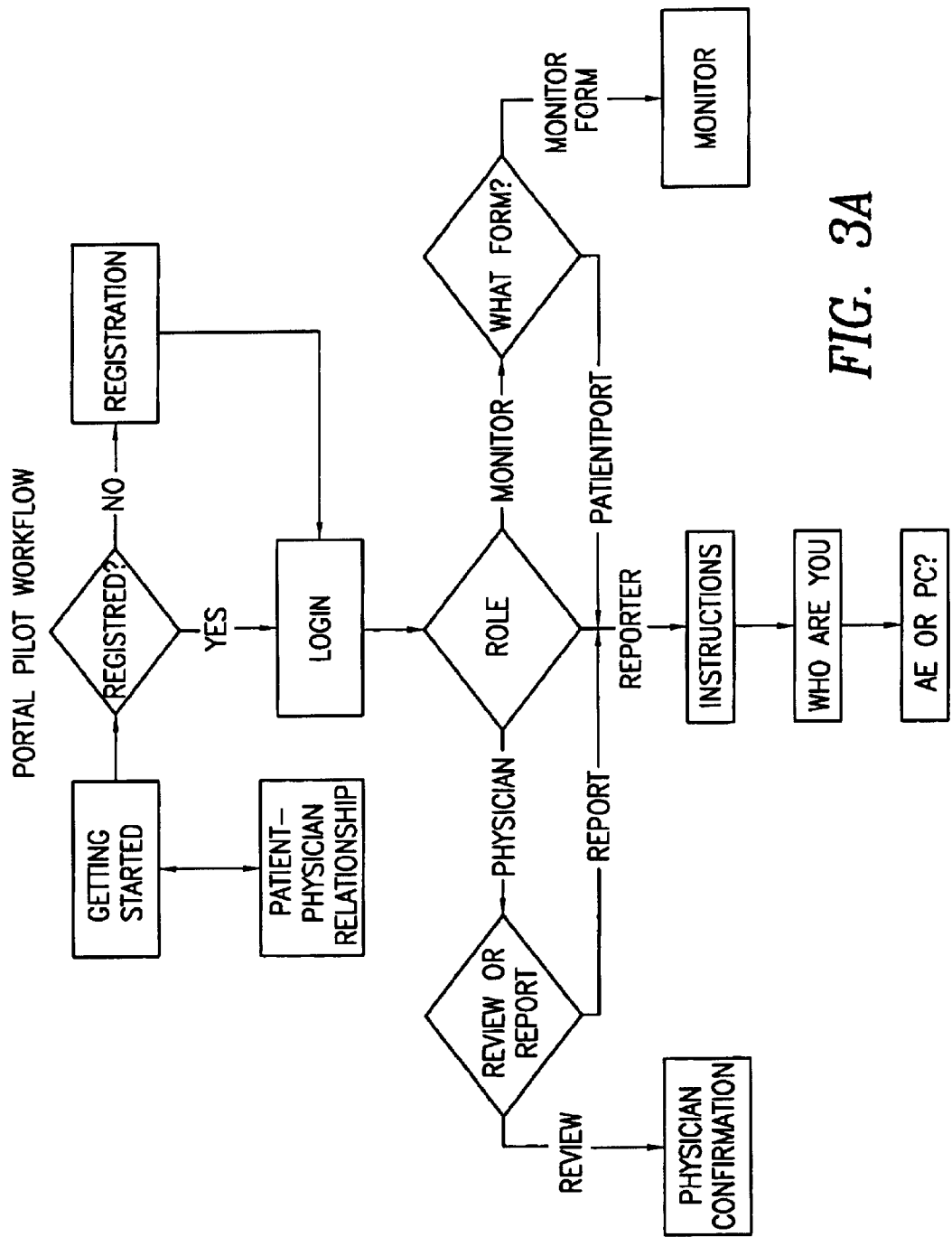
FIG. 3a is a flow chart depicting a detailed exemplary site flow diagram for the present invention.
Figure 3B:
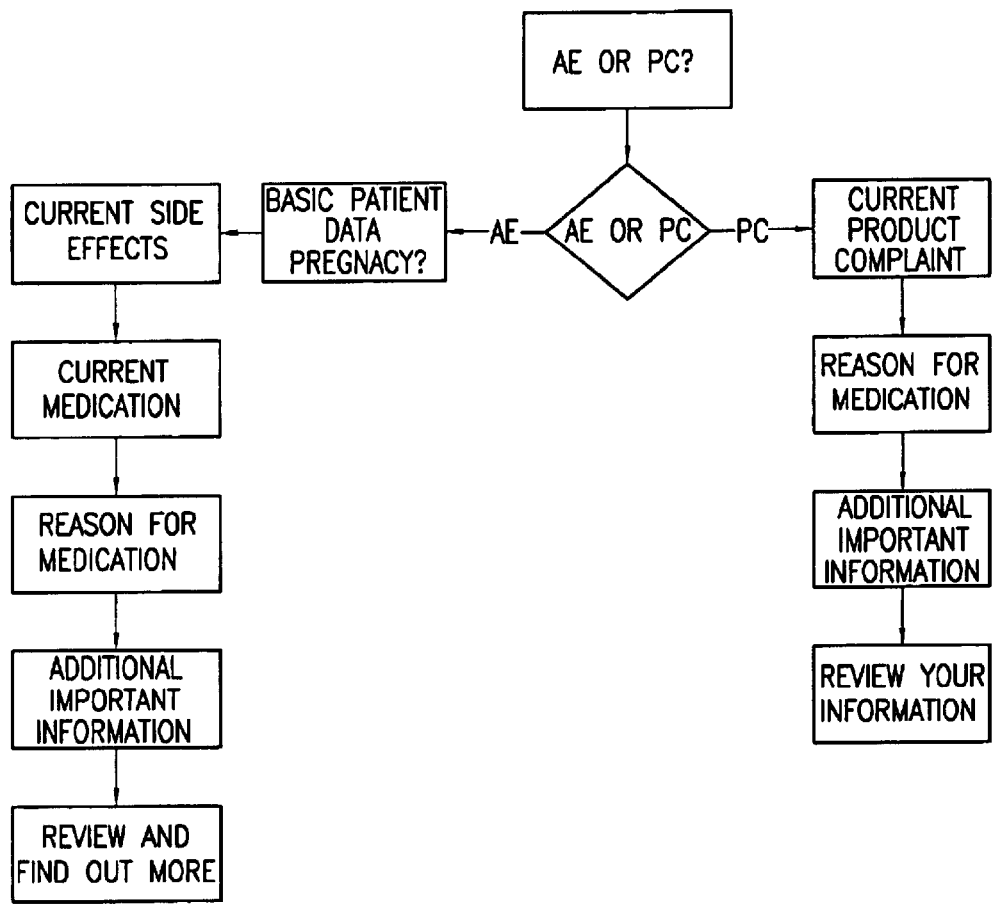
FIG. 3b is a flow chart depicting a detailed exemplary site flow diagram for the present invention.
Figure 3C:
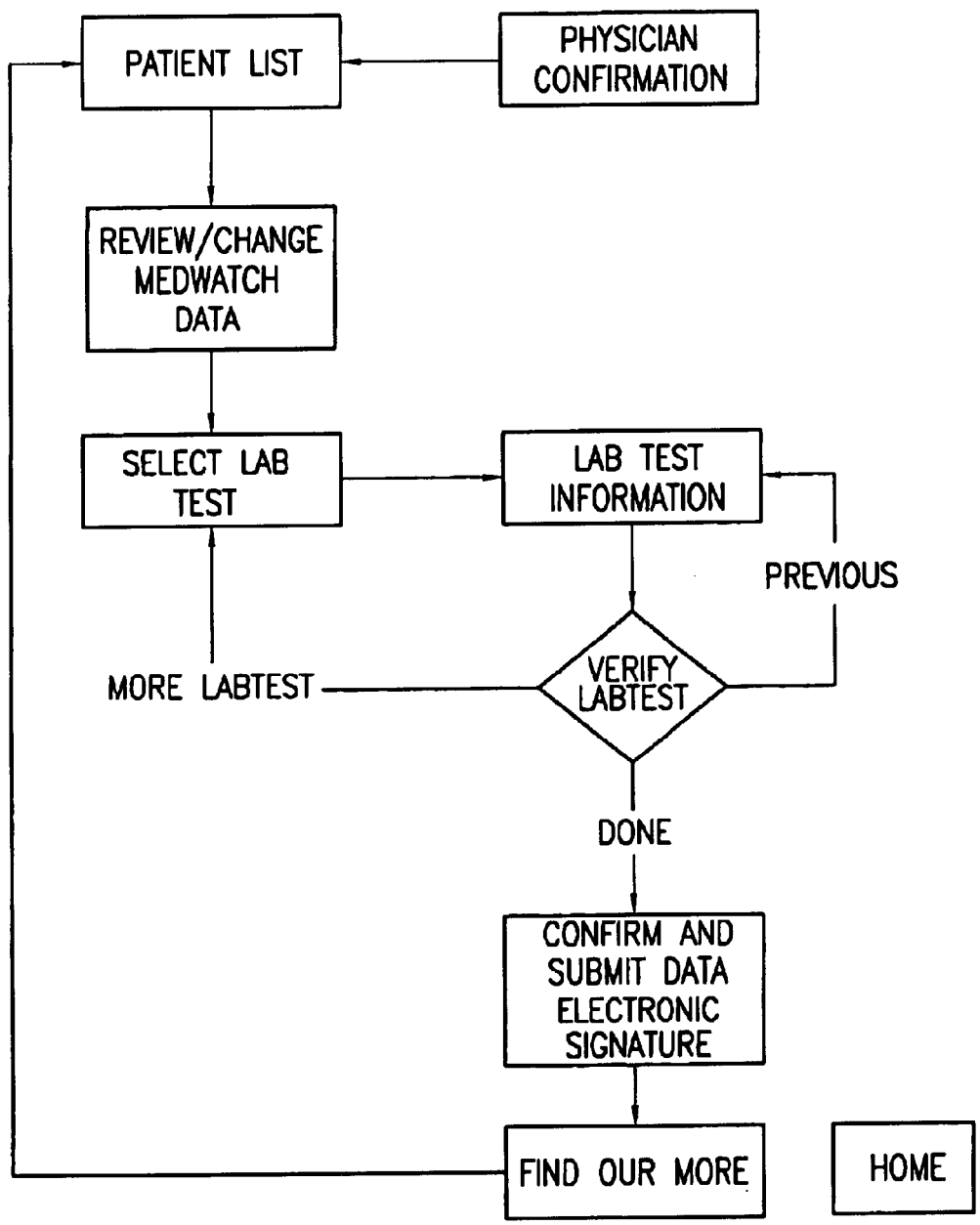
FIG. 3c is a flow chart depicting a detailed exemplary site flow diagram for the present invention.
Figure 3D:
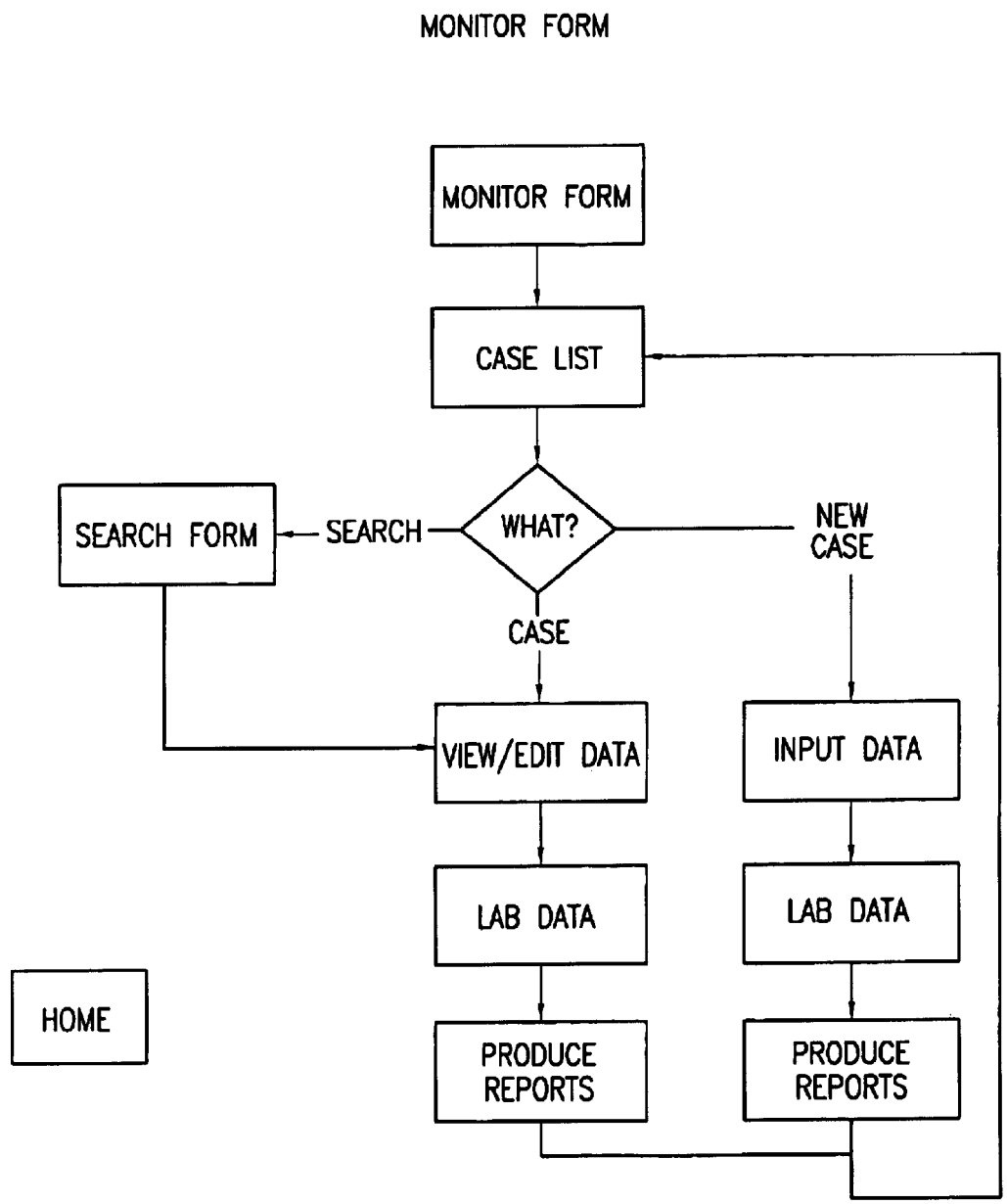
FIG. 3d is a flow chart depicting a detailed exemplary site flow diagram for the present invention.

A more detailed-view of the interface workflow is shown in FIGS. 3a–3x. Turning now to FIG. 3a, there is shown an exemplary Portal Workflow diagram. The user, upon accessing the site will be presented with a Getting Stated page, which has a link to a page presenting patient physician relationship information for the user. After accessing the Getting Started page, the interface business logic directs the user through the registration and login process. After the user has completed the registration and login procedure, the user selects either the Physician, Reporter or Monitor path. As can be seen in FIG. 3a, the Physician and Monitor path can alternately follow either a review path, i.e. Physician confirmation or Monitor, or can be redirected to the Reporter path. The user then proceeds to enter identity information and indicate if an Adverse Event or Product Complaint will be entered. Turning now to FIG. 3b, there is shown a workflow diagram for Adverse Event and Product Complaint reporting path. The interface of the present invention directs the user through the selected path to collect information regarding the event being reported. FIG. 3c depicts the interface workflow for the Physician confirmation path. Upon selecting the Physician Confirmation path, the physician can select a particular patients report from a list and then review and or change data on that report. Additionally, the physician can select, review and verify lab test result information entered by the reporter. Upon completing his review, the physician can confirm the data and submit the data along with an electronic signature. The physician can then review additional patient reports or end his session. Turning now to FIG. 3d, there is shown an exemplary workflow diagram for the Monitor path. Upon accessing the Monitor path, the user can review a list of cases and select from that list. The user can then; search the reported cases for particular data, view and edit previously entered data, input new data and produce case reports.

Figure 3E:
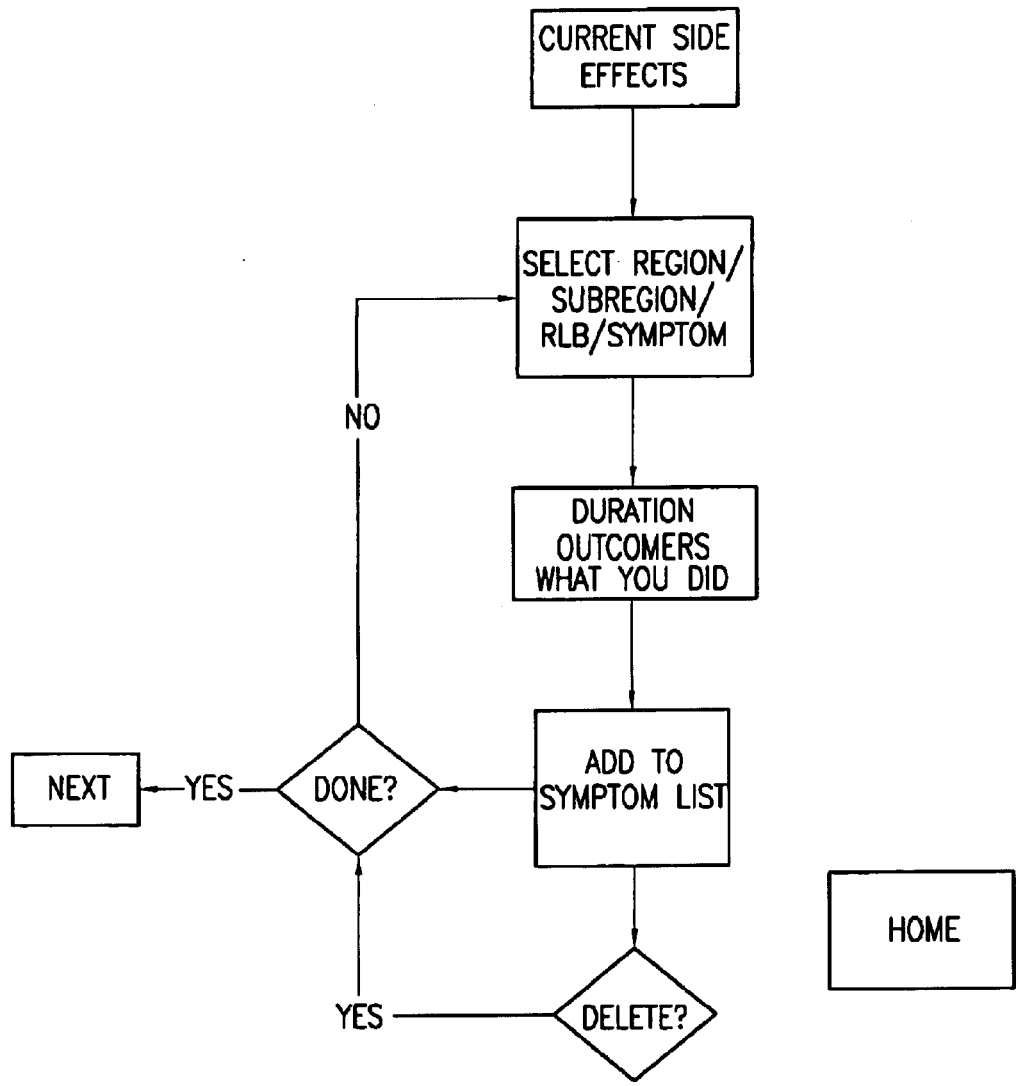
FIG. 3e is a flow chart depicting a detailed exemplary site flow diagram for the present invention.

Turning now to FIG. 3e, there is shown a detailed view of the side effect reporting workflow of the Adverse Event reporting path. The user is directed through the side effect reporting path to provide information regarding the particular body region, sub region, symptom, duration and outcome of at least one side effect.

Figure 3F:
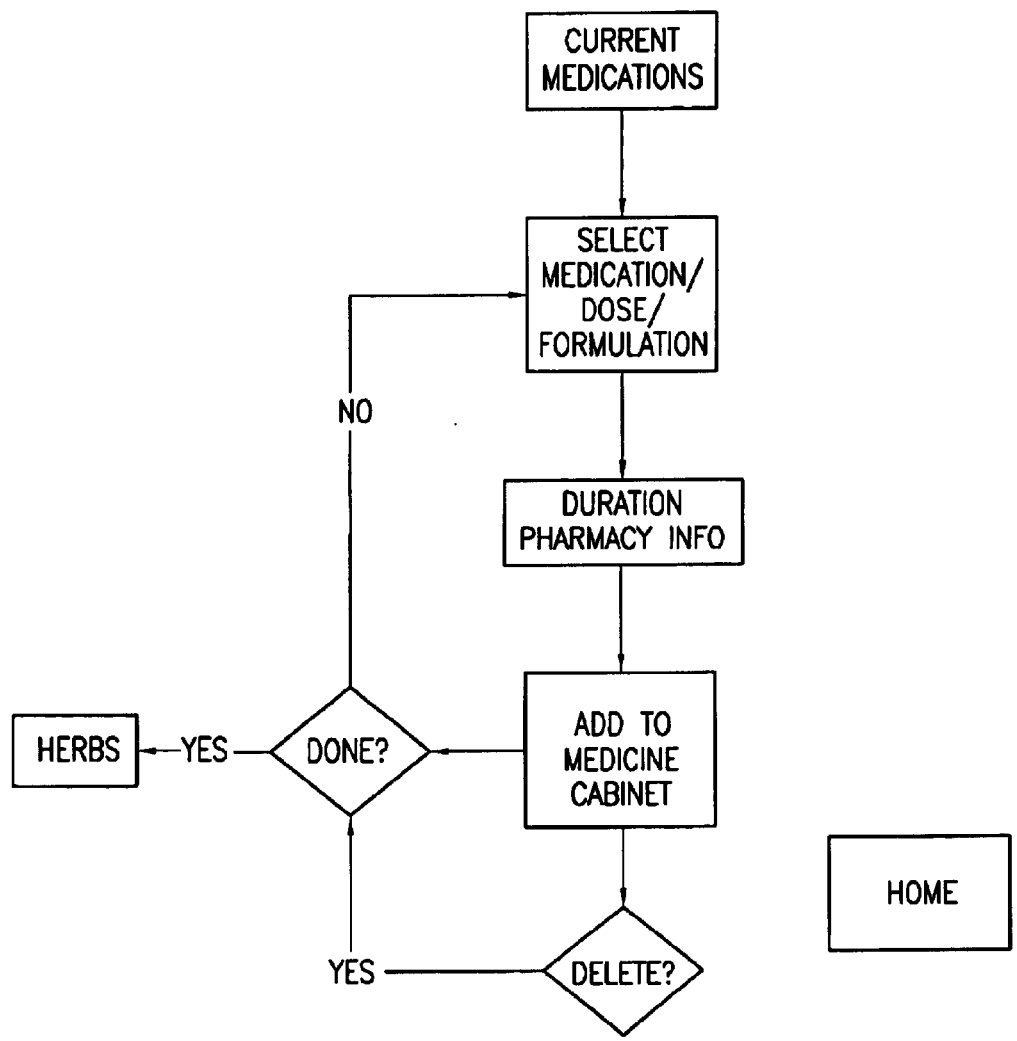
FIG. 3f is a flow chart depicting a detailed exemplary site flow diagram for the present invention.
Figure 3G:
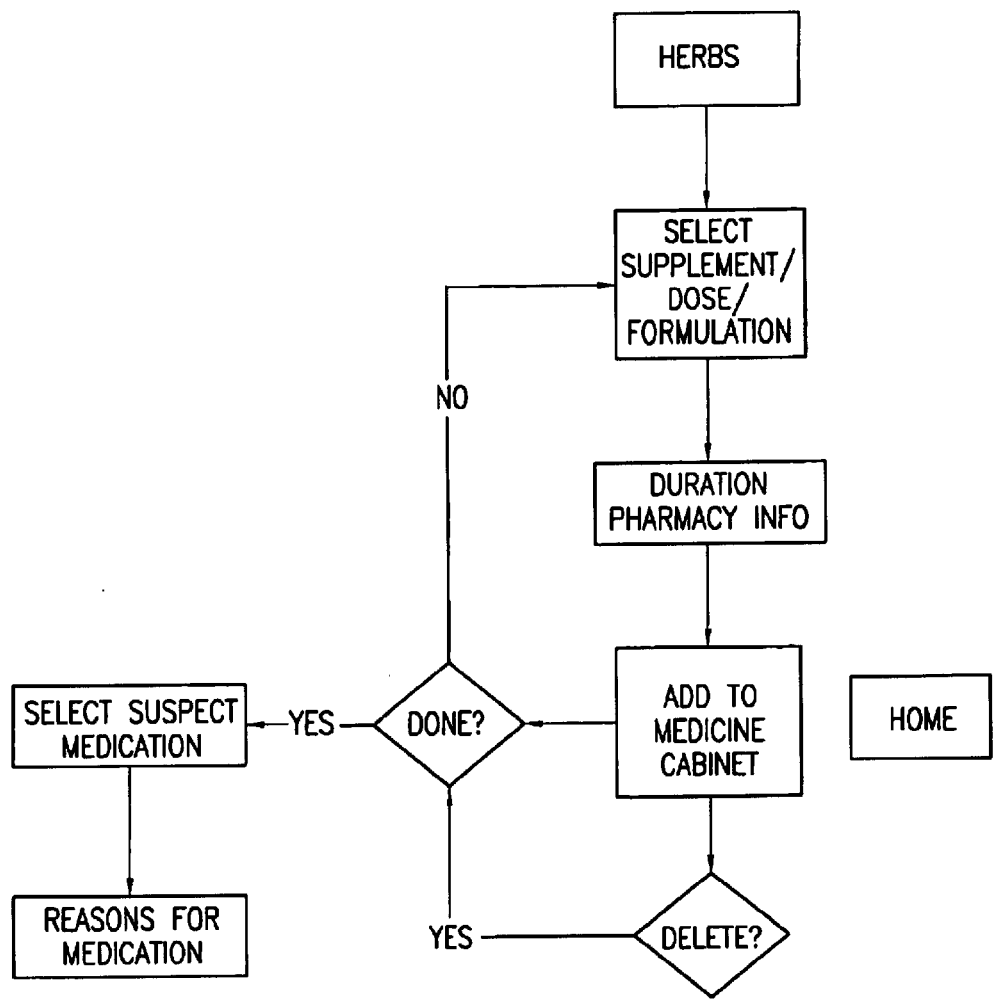
FIG. 3g is a flow chart depicting a detailed exemplary site flow diagram for the present invention
Figure 3H:
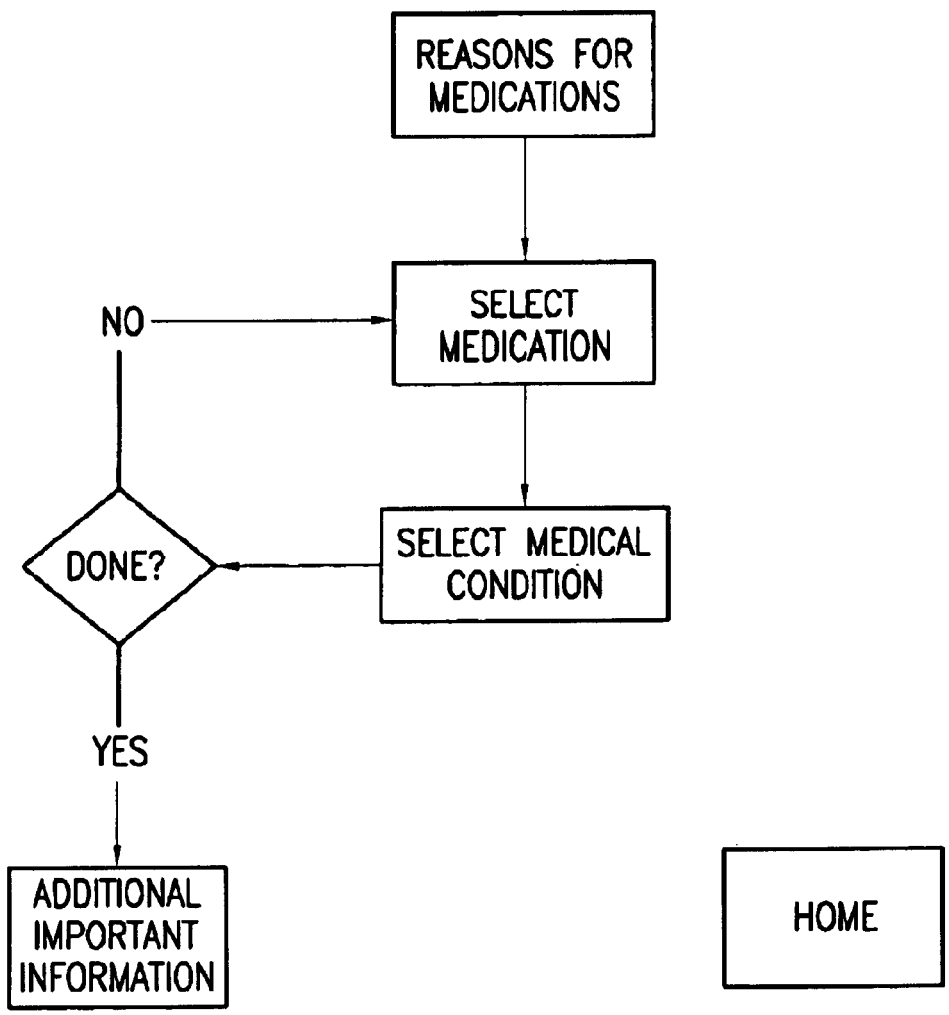
FIG. 3h is a flow chart depicting a detailed; exemplary site flow diagram for the present invention.
Figure 31:
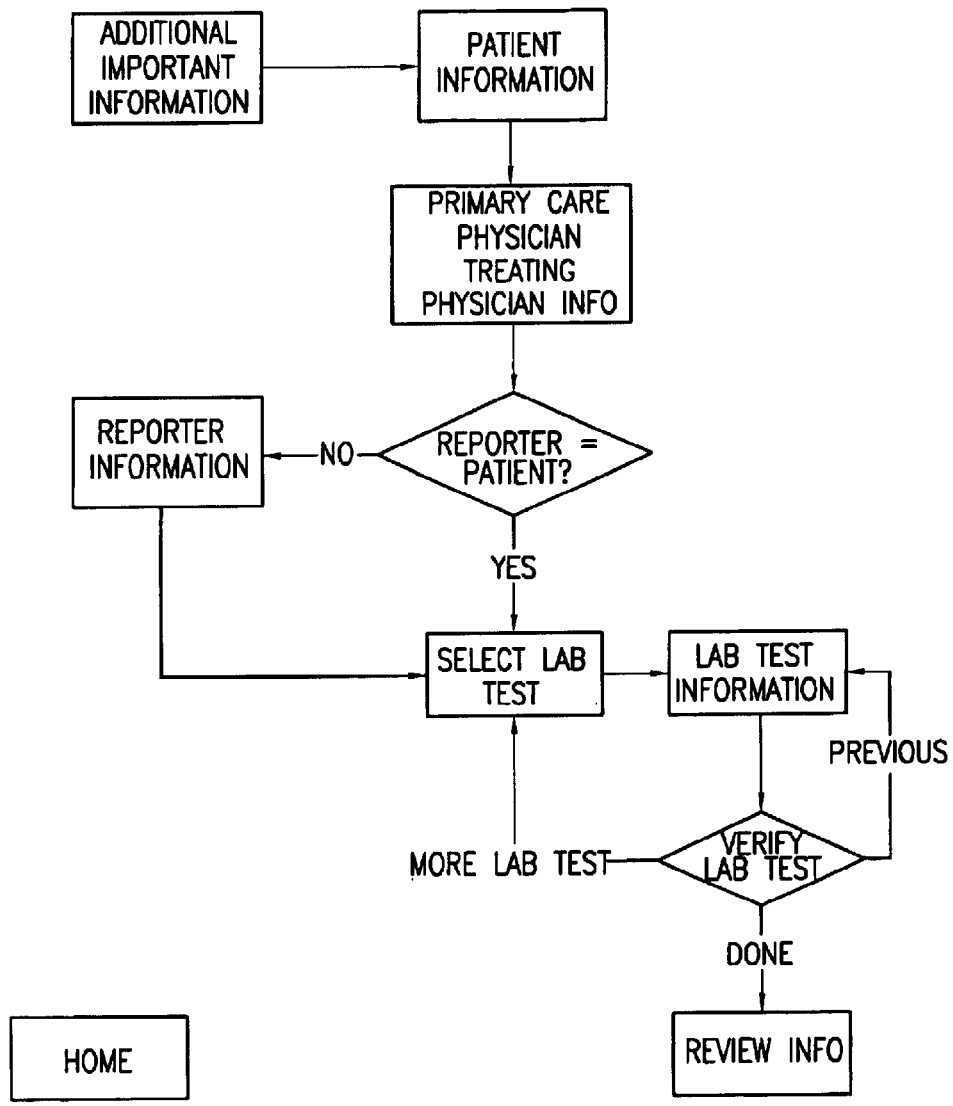

Turning now to FIG. 3f, there is shown a detailed view of the Current Medication reporting workflow of the Adverse Event reporting path. As shown, the user is directed to provided information regarding current medications, including dosage, formulation, and duration and pharmacy information. Upon completion, the user is can add the medication to a Medicine Cabinet for inclusion in the final report and proceed to Herb and Nutritional reporting or delete the information. In FIG. 3g, there is shown a detailed view of the Herb and Nutritional Reporting workflow of the Adverse Event reporting path. The workflow of this portion of the interface is similar to the Current Medication workflow, however is used to supply information regarding herbs and nutritional supplements rather than medication. Additionally, upon completion, the user must supply information regarding the medication suspected of causing the adverse event, and the reason for taking the suspect medication. FIG. 3h, depicts a detailed view of the Reasons for Medication workflow of the Adverse Event reporting path. The user is directed to indicate the medication suspected of causing the Adverse Event and the medical condition for which the medication is being taken. Finally as shown in FIG. 3i, the user must supply and review additional important information regarding his or her primary care physician or treating physician, reporter information and lab test information.

Figure 3J:
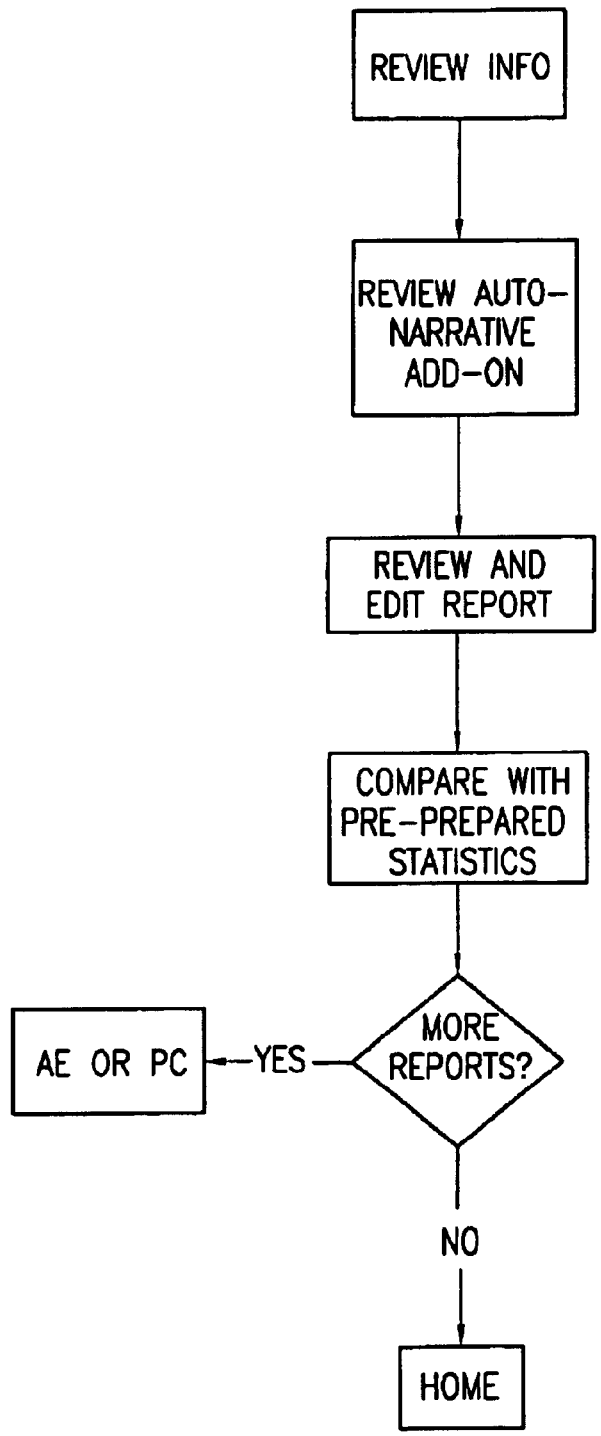
FIG. 3j is a flow chart depicting a detailed exemplary site flow diagram for the present invention.
Figure 3K:
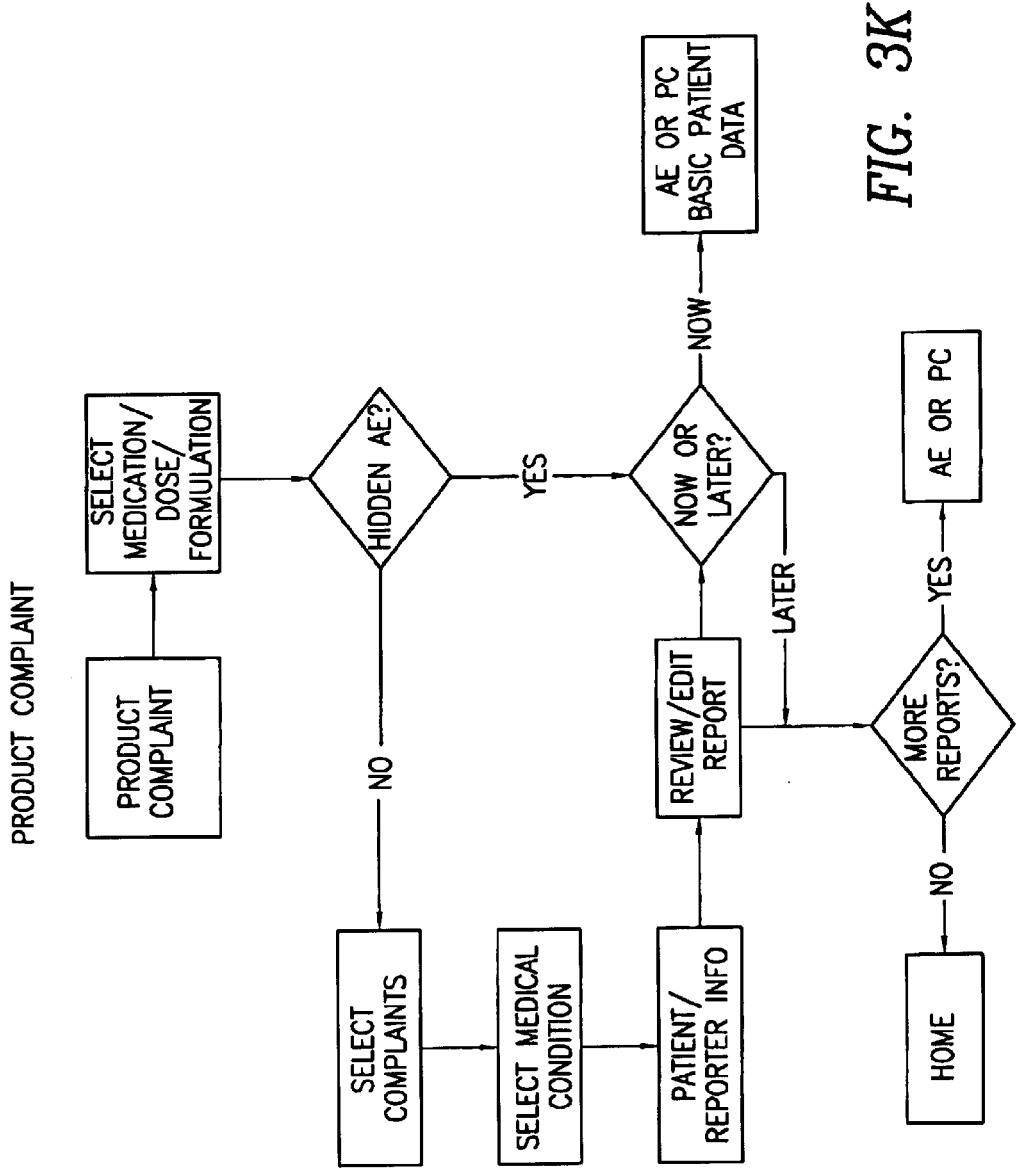
FIG. 3k is a flow chart depicting a detailed exemplary site flow diagram for the present invention.

Turning now to FIG. 3j, there is shown a detailed view of the Review Information and Find Out More reporting workflow of the Adverse Event reporting path. As depicted in FIG. 3j, the user must review the information supplied, the auto narrative and the summary report. After comparing the report with pre-prepared statistics, the user can enter additional Adverse Event Reports or Product Complaints.

Turning now to FIG. 3i, there is shown a detailed view of the Product Complaint Workflow. The user is first directed to provide information regarding the product in question such as medication dosage and formulation. Additionally, the user is asked to indicate if there is an Adverse Event associated with the Product Complaint. The user can be prompted to enter the Adverse Event data as well as the Product Complaint. If there is no associated Adverse Event, the user is directed to indicate the product complaint. Product Complaints can be in several categories, for example "Did Not Work"; "Did Not Like", i.e. "Color";

"Something Wrong", i.e. "Package Damaged" and other such information. As in the Adverse Event reporting path, the user must also supply identity information and review and confirm the data supplied.

Figure 4:
FIG. 4 is a depiction of an exemplary version of a "Registration" page

Turning to FIG. 4 there is shown an exemplary version of a "Registration" page. The Registration page displays free form data entry fields for collecting identity information from a first time user. Those fields include in an exemplary version; First Name, Last Name, User ID, Password, Password again, and an additional security devise such as a Secret Question, Secret Answer (a question and answer preselected by the user in order to provide a means to confirm the users identity), phone number and E-mail address. Also included on the registration page will be a statement informing the user that their consent is needed to contact the users physician to gather additional information to complete the report. The user is required to provide this consent by clicking an Accept button before proceeding with the form. A menu of "Getting Started" steps for a first time or previously registered user is also provided comprising links to the different pages within the site that the user can select to proceed to the desired login or registration step.

Previously registered users will be directed to a login screen. FIG. 5 illustrates the display of a Web page depicting an exemplary version of a user login page for the interface of the current invention. As depicted on the flow chart once the login is complete, the user can select the patient, physician or monitor reporting path.

To begin the reporting process the user is first directed to a page as depicted in FIG. 6 which informs the user that both patient and physician identification information is required to adequately complete the reporting process. The user is reminded to include such information on the registration page. The user can then begin reporting an Adverse Event or Product Complaint or complete a report that was previously started by clicking the appropriate button provided.

Upon starting a new event report or restarting a report that was started at a previous time the user is presented with an Instructions page. FIG. 7 illustrates the display of an exemplary Instructions page for the interface of the present invention. The instructions indicate to the user the steps needed to report in this embodiment either a Side Effect or Adverse Event, or a Product Complaint, although the instruction page could include additional information helpful to the user.

Figure 8:
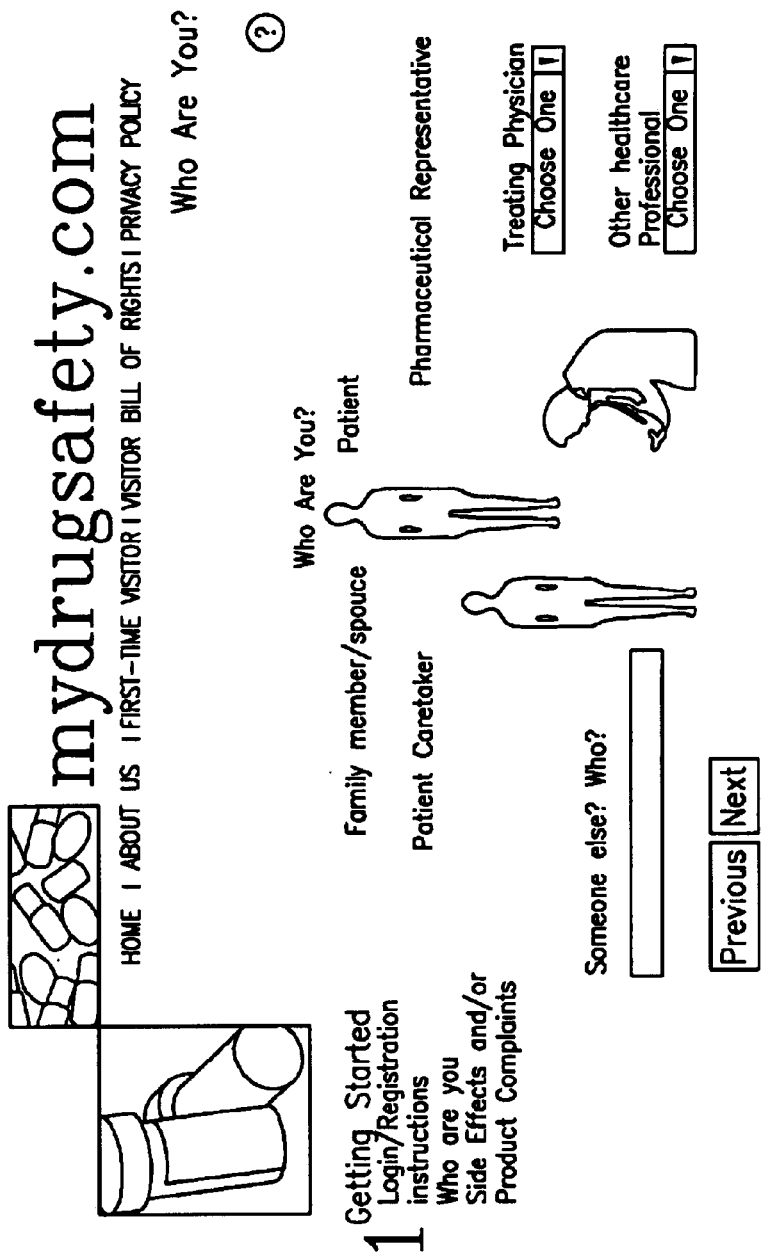
FIG. 8 is a depiction of an exemplary depiction of a user identification page.

FIG. 8 is a exemplary depiction of a data input page where the user can select a link or input data by a free form data field or a pull down menu with respect to the his or her identity. The page includes links for Patient Caretaker, Family Member/Spouse, Patient, Pharmaceutical Representative, Treating Physician or Other Healthcare Professional. In addition, there is provided a data entry field for users to enter identity information that is not one of the available categories. Upon selecting one of the links or pull down menu options the user is then directed to the appropriate page for event reporting. In that way the user is directed to the data intake page that is most appropriate to his or her role with respect to the event to be reported.

Turning now to FIG. 9, there is depicted an exemplary version of a page wherein the user can designate if the report being made is an Adverse Event or a Product Complaint. After selection of either a Product Complaint or Adverse Event report, additional fields will be presented to the user, wherein additional information such as Age, Height, Weight, Gender and Pregnancy are entered. After entering this data, the user is presented with the appropriate reporting page for either Adverse Events or Product Complaints.

Figure 10A:
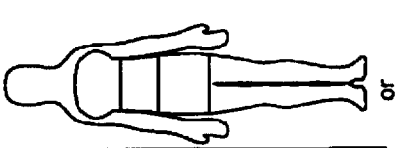
FIG. 10a is a depiction of an exemplary Adverse Event reporting page.
Figure 10B:
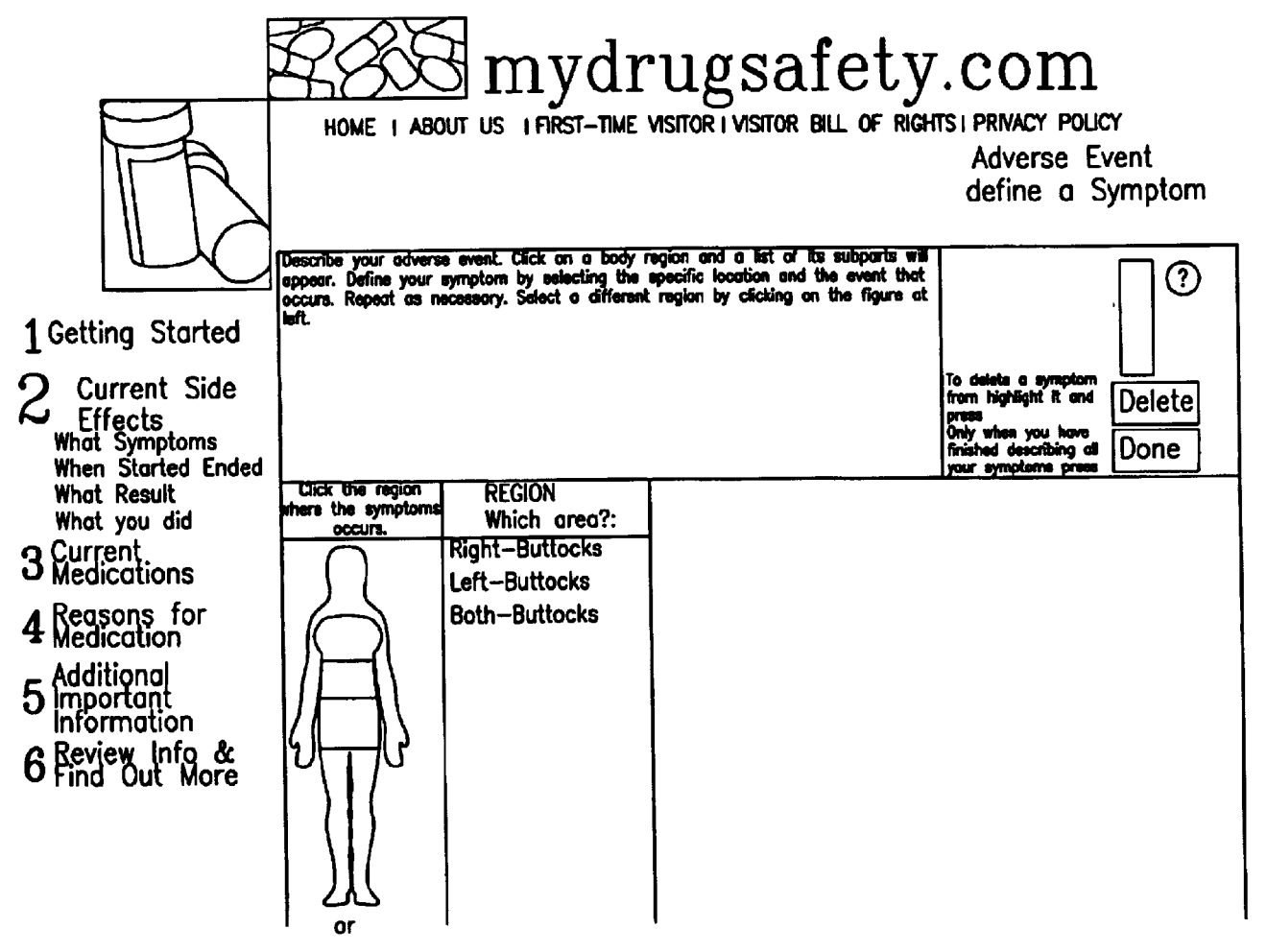
Figure 12:
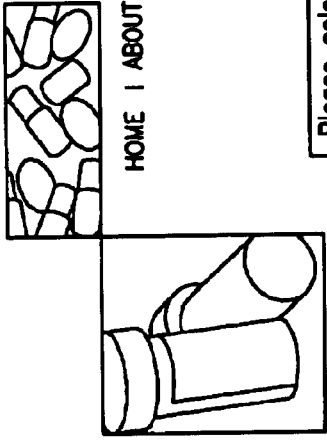
FIG. 12 is a depiction of an exemplary suspect medication reporting page.

FIG. 10a depicts an exemplary version of an Adverse Events reporting page. On the Adverse Events reporting page the user has several fields in which to input Adverse Event information. Included in the data that the user must input are the Adverse Event symptoms. The symptoms list contains popular names for events that a patient would use to describe their condition. The user can scroll through the list to select the symptom or symptoms that most accurately depict the Adverse Event. In addition, there is provided a diagram depicting a human body. The diagram is divided into regions that represent links for displaying symptoms for each region of the body. For example, one can select the shoulder and arm region link on the body diagram. After selecting a particular region, a sub region list will be presented to the user, as shown on FIG. 10a, where the user can more specifically delineate the region of concern. For example the user can designate the right, left or both sides of a selected region. Upon designating a body sub region there will then be displayed symptoms, which are pertinent to that body sub region that the user can select by clicking as shown on FIG. 10b. The symptoms are listed using popular names for each symptom. Each popular symptom description is linked or hard coded to the standardized medical dictionary term and code for that symptom. As shown on FIG. 10c, the user is asked to indicate the duration of any symptoms by inputting the date that any symptom started, the date that a symptom ended and further indicate if the symptom is ongoing. The user must also enter information regarding the end result of the Adverse Event such as hospitalization or death of the patient. Finally, the user is asked to provide information regarding what action was taken in response to the Adverse Event. The user is presented with several choices that can be checked to indicate a particular action, such as Did Nothing, Consulted a Physician, Stopped Medication, Reduced Dose or Switched Medication. With respect to the Reduced Dose or Switched Medication data input choices, the interface provides the user with free form data entry fields for providing the necessary information. Furthermore the user is provided with a check box to affirm if the actions helped, a check box to indicate if the effect returned when medication was resumed, if another medication was taken against the Adverse Effect and a check box to indicate if the additional medication was effective. Finally there is provided a free form data entry field to indicate any alternate remedies that the patient pursued. Of course this data entry selections and graphical diagrams can be modified to customize the interface for use in a particular application. One such modification is depicted in FIG. 10d. FIG. 10d shows an exemplary adverse events reporting page displayed using the German language. The interface of the current invention can be modified to display all text in any language. Furthermore, the interface can be modified to display pharmaceuticals and products available in a particular market. In addition to changing the language, the interface can be further modified to reflect local differences in pharmaceutical products, description of symptoms, and other differences. Therefore, FIG. 10d is meant to exemplary only, one skilled in the art could see that it would be possible to incorporate a change in the language of the interface, as well as other modifications while maintaining the functionality of the invention.

Figure 11:
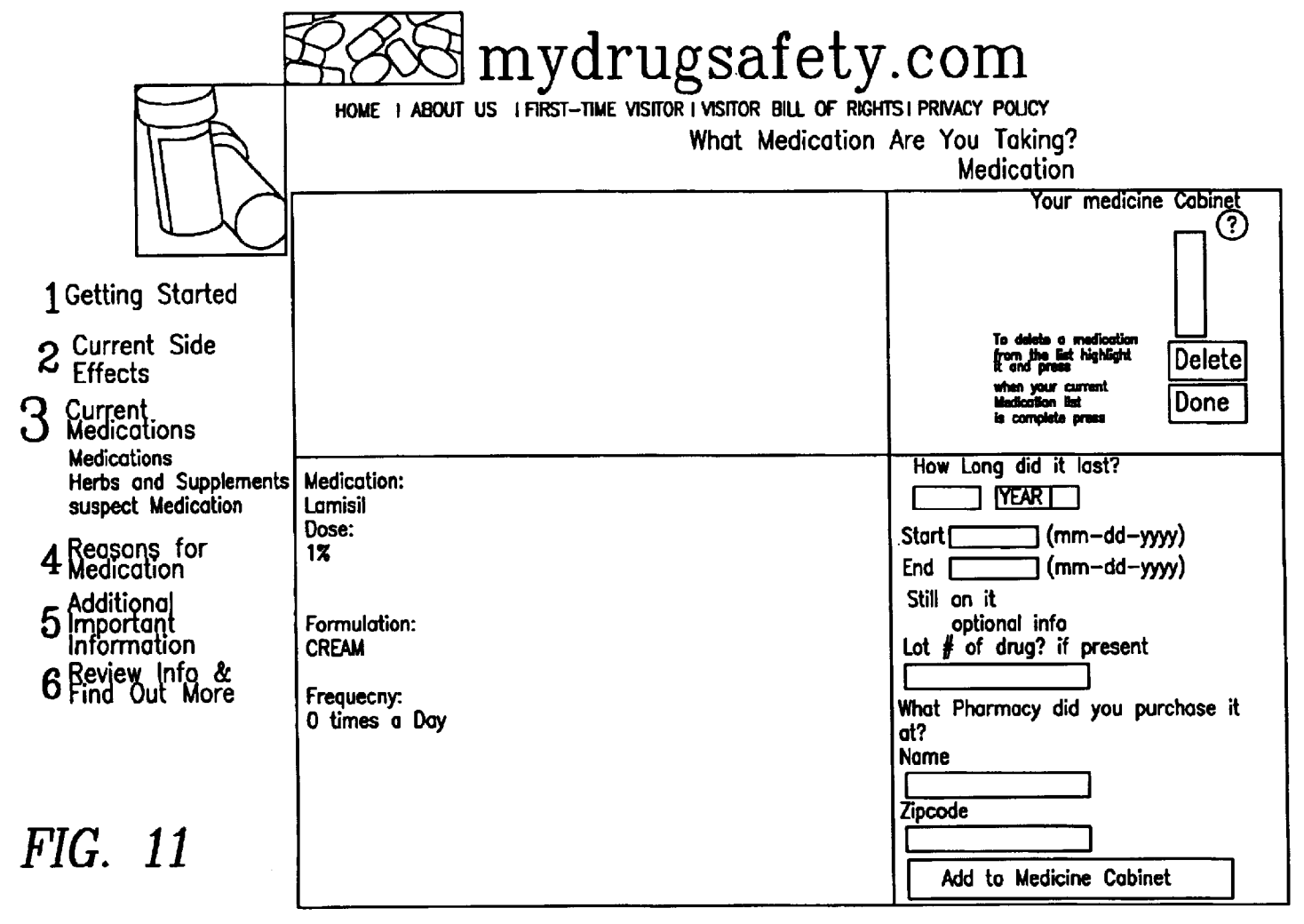

Turning now to FIG. 11, there is depicted a data entry page for the user to enter information regarding the medications that the patient is taking. There is provided an index of medication names that the user can click on in order to select the medication that they are taking. Alternately the user can select the medication from a pull down menu or enter the medication name in a free form data entry field. The medication list in comprised of all commercially available medications. In addition, each listed medication can include a graphic depiction of the medication, in order to assist the user in selecting the correct medication from the pull down menu. The user must also provide the dosage and formulation information by selecting from a pull down menu.

After the user has selected the medication, dosage and formulation information and provided the information regarding length of usage time and optional information the selection is recorded and displayed in a data field on the page known as Your Medicine Cabinet by the user clicking on a button to add the medication to the list of medications. Once the user has entered a first medication into the Medicine Cabinet, he or she can repeat the process to add another medicine, delete a medicine from the list by selecting and clicking on the delete button or indicate that he is finished entering medications to the list by selecting the Done button. Additionally in FIG. 12 there is shown an exemplary web page where a user must select the medication or medications, which are suspected of causing an Adverse Event. Displayed on the page is a list of the medications that the user has previously indicated are being taken. Each medication listed is listed together with a check box. The user is prompted to enter a check in the box of for each medication that is believed to have caused an Adverse Event. Once the user has indicated which medication is suspected of having caused an Adverse Event, additional information is requested from the user regarding the medical condition of the patient with respect to the use of the medication. In that way it is possible to include in the database information regarding what is known as "off-label" use of a medication, i.e. use of a medication for a non-indicated condition.

Figure 13:
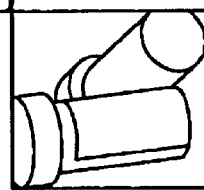
FIG. 13 is a depiction of an exemplary medication supplement-reporting page.

Similarly as depicted in FIG. 13 there is provided a data entry page having the same data fields and as that depicted in FIG. 11, however it is intended for the user to provide data related to herbs or nutritional supplements that the patient may also be taking in addition to any prescribed medication. This information is important in evaluating the Adverse Event, as there may be a contraindication between a medication and a nutritional event.

Turning to FIG. 14 there is shown a web page where a user can indicate the medical condition for which a medication has been prescribed. The medications that the patient is taking may have been previously indicated as the suspected source of the Adverse Event are listed on the page; the user can then select from a pull down menu the medical condition for which the medication is prescribed. The pull down menu lists only the on-label uses for each medication. If the condition is not listed on the pull down menu, then the user can enter the condition via a free form data entry field. As described hereinafter, when a condition is entered in the data entry field, the entry is flagged in the database for further review by a safety monitor. After the user enters the information indicating the disease for which the medication is prescribed, they are then directed to either the patient or physician information page. If the user is the patient, then the patient information would have already been entered and the user will be directed to the physician information page, conversely if the user is the physician, then the physician information would have already been entered and the user will be directed to the patient information page.

Figure 14A:
FIG. 14a is a depiction of an exemplary laboratory test reporting page.

In the same way that the information is gather regarding Adverse Event symptoms and medication, the interface of the present invention could be modified to further include web pages to collect information regarding any diagnostic tests performed on the patient with respect to the Adverse Event. This could include laboratory tests. FIG. 14A depicts an exemplary page for reporting the results of Laboratory test results associated with the report of an adverse event or product complaint. Of course the method of the present invention is not limited to collecting information regarding any particular diagnostic test and could be modified to accommodate a particular circumstance.

Turning now to FIG. 15, there is depicted a page displaying a verbatim narrative that is compiled from the information provided by the user. The narrative is generated by the narrative engine that is part of the software embodying the present invention. The narrative engine uses the response that the user has input and formulates a highly structured and standardized narrative of the Adverse Event. The narrative engine employs programming logic that would be well known to one skilled in the art. The narrative provides an additional means of quality control for the event report by reiterating the users input in a standardized, structured, clear and concise manner. The user is given an opportunity to review all of the information provided in the form of a written narrative and add or correct any information.

Figure 16C:
FIG. 16 is a depiction of an exemplary summary report.

After reviewing the narrative report, the user is given a final opportunity to verify the information provided. FIG. 16 depicts a page displaying a summary report of all information previously entered. The information includes Patient Information, Adverse Event information, Suspected Medications and Concomitant Medication. The user is instruction to type over text to edit any information appearing in the summary and then indicate that the report is complete by clicking on a button provided. Finally the user is presented with a page displaying data fields for entering identification information for the user. Information such as user name, address, telephone number, date of birth and occupation are typically included.

In accordance with the description of the above information gathering pages of the interface of the present invention, there is also provided within the patient reporting process a path to report Product Complaints. While the information gathered will not be exactly the same as that collected for an Adverse Event, modifications to the interface and database of the present invention will be obvious to one skilled in the art. Likewise the interface also provides a physician path and a monitor path. These paths differ from the patient path in that the main function of each is to provide information to a safety monitor or a patient's physician. Therefore the interface is adapted to report information that has been previously entered in the physician and monitor path.

III. Database Terminology Standardization

The Adverse Event and Product Complaints that are furnished by the user are input using common popular terms for each symptom in accordance with the vernacular language of a particular country or culture. It is however, necessary to describe all symptoms in standardized terms in the final report the pharmaceutical company uses in assessing an event. For example, symptoms can be described using MedDRA terminology to ensure that like events are described in like manner. However, due to the large number of terms in standardized dictionaries such as MedDRA, it is difficult to efficiently encode the description of an Adverse Event or Product Complaint.

The standardized terms that are presented to the user are compiled in such a way so as to correspond to everyday common terminology used to describe symptoms. Thus rather than utilizing a symptom list derived from a standardized industry dictionary such as MedDRA, the symptom list is compiled by first generating a list of commonly used terms to describe a symptom. Those terms are then hard coded to correspond to a single particular standardized symptom term. In this way, the user of the present invention is presented with an interface that is easier to use and thus results in more reliable reporting by the user.

IV. Database

Turning now to the database component of the present invention, there is provided a database with a software component for managing and storing data that is transmitted from a user to the host computer embodying the present invention. Utilizing the Internet to collect and manage data allows an enterprise to quickly and efficiently connect to many and distant remote users, however, a number of problems occur when using a Internet base data management system which are not addressed by the current systems.

A data management system utilizing Internet-based communication is different from mainframe and client-server arenas traditionally used for data management. One difference is that HTTP, an underlying protocol of internet communication, is both connectionless and stateless.

The Internet is said to be stateless because no information about what occurred previously is maintained. Most modern applications maintain state, which means that they remember what you were doing last time you ran the application, and they remember all your configuration settings. This is extremely useful because it means you can mold the application to your working habits.

The World Wide Web, on the other hand, is intrinsically stateless because each request for a new Web page is processed without any knowledge of previous pages requested. This is one of the chief drawbacks to the Internet and the HTTP protocol. Because maintaining state is extremely useful, programmers have developed a number of techniques to add state to the World Wide Web. These include server APIs, such as NSAPI and ISAPI, and the use of cookies.

The stateless condition of the Internet causes a problem for dynamic interactions where a web system needs to be able to keep track of the user's state during a session involving multiple web interactions (e.g., web page requests). Without a way to manage state, between web transactions the system will have "forgotten" information about the user and the context of the session. This can be further complicated by the fact that in many large web systems the user does not interact with the same web server during a session.

The stateless condition is especially a problem when using the Internet for collecting data. When collecting complex data using an Internet based application, it is usually necessary to have multiple web pages within a site for identifying and registering a user, collecting data and confirming user input. This is a problem in a stateless environment, because information entered identifying the user or data collected on one page is lost when the user directs his browser to another page, unless that information is saved directly to a database or cookies are used. Saving information directly to a database as soon as it is entered is an inefficient process and can result in incorrect data being included in the database.

The present invention overcomes the traditional problems of using a stateless environment for data management by utilizing a software data management tool for receiving, managing and storing data.

All data collected from the user in the current invention is stored in a database that includes the user and patient identity information as well as the incident report. The database makes use of an XML encoding because of its capability to create large repositories of data that operate across any computer platform. For example one can map the fields of a database to elements, and then share that information across a vast array of platforms. The XML database structure is hosted on the server side and then the XML is completely decomposed into HTML interface components (form elements) at the application server and sent as HTML to the client where it is rendered.

The XML data structure provides an extremely flexible architecture for structured information collection, manipulation and storage. The interface portal of the present invention implements a data collection mechanism, which moves users from page to page, enforcing business logic (such as ensuring that required fields have content) and populating that data to an XML structure. As each page is completed, the XML structure is serialized and moved to the next page where it is deserialized and the next page's content is loaded into the structure. When a person has completed the required information, the XML structure is deserialized, each data field is inspected to ensure that the data conforms to specified constraints, and the information is entered into the system. The entire populated XML structure is also stored in the database and used to quickly populate screens when monitors or other medical personnel request the file.

The flexibility provided by using XML to manage the data allows the Portal and collected data to be highly modifiable. While data is deserialized and stored discreetly in the database, that data is really only used for quick searches. The actual work is performed through the passing, storage, and manipulation of the XML structure.

Furthermore, in another embodiment, it would be possible to implement the present invention by utilizing signing certificates. It would be possible to actually send a user the XML structure so they can sign it. The signed objects could then be stored in the back end for non-repudiation.

Figure 17:
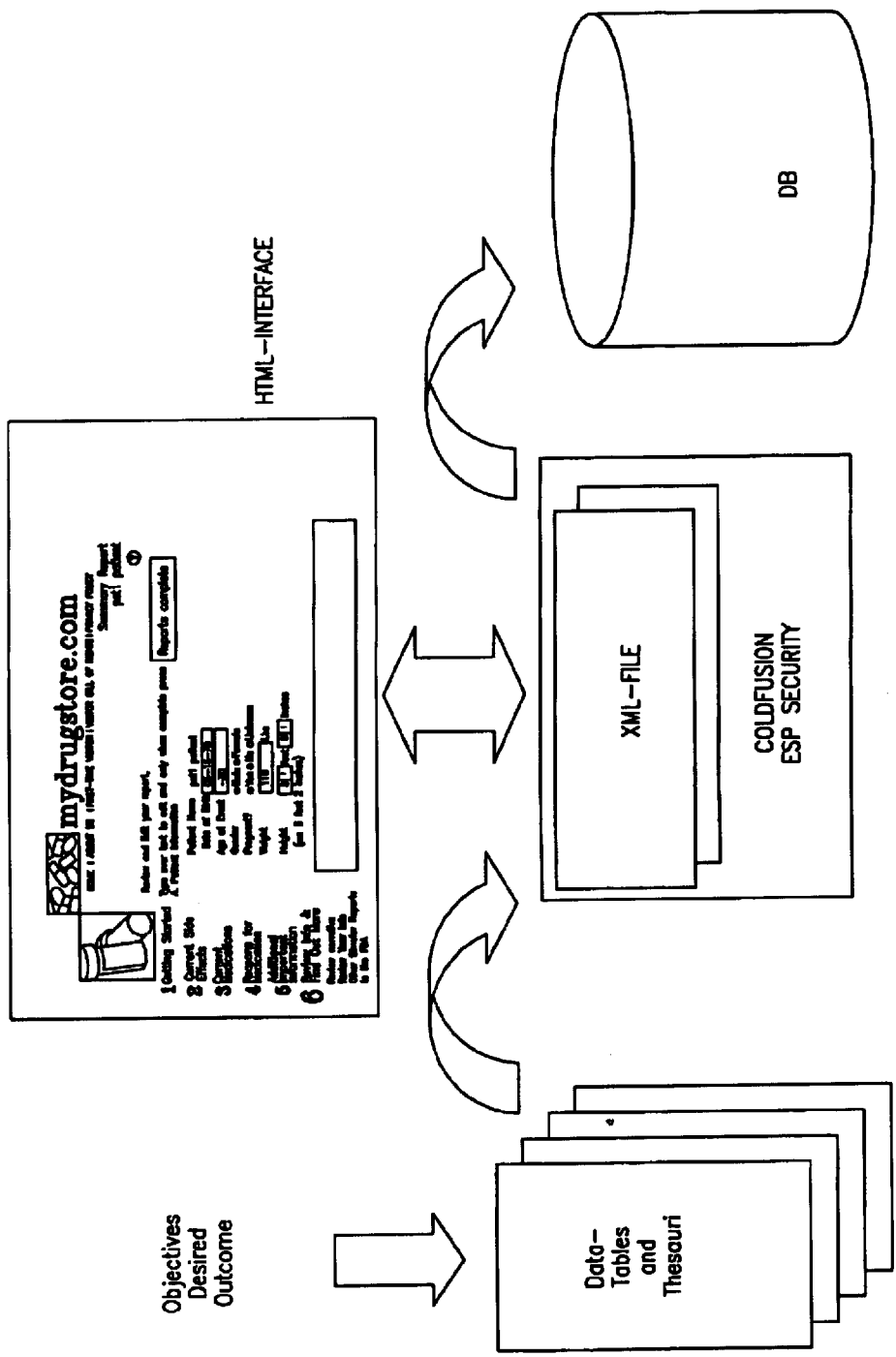
FIG. 17 is a depiction of a data flow diagram of the present invention.

Turning to FIG. 17, there is depicted a block diagram representing components of the system of the current invention for the transfer and storage of data. The system is depicting as including a user interface, a software package, commonly referred to as "middleware" that controls the flow of data between the user and the host, including logic and data checking. In addition there is provided a thesauri database, a user database, and an event report database.

There is shown in FIG. 17 an exemplary interface screen, the interface software and logic, and a plurality of database storage media. The interface includes a plurality of data entry categories such as symptom, medication-dosage, and medication-indication. A user enters data using the interface through a plurality of pull down menus or free form data entry fields. It is preferable that the user enter all data by selecting an entry from the provided pull down menus, therefore it is a feature of the present invention to include a full range of pull down menus to cover a majority of the possible data entries for each category. In that way it is possible to reduce input errors by providing the user with a list of the most common data entries. Therefore a user will only need to enter data without the aid of a pull down menu in exceptional circumstances.

Figure 18:
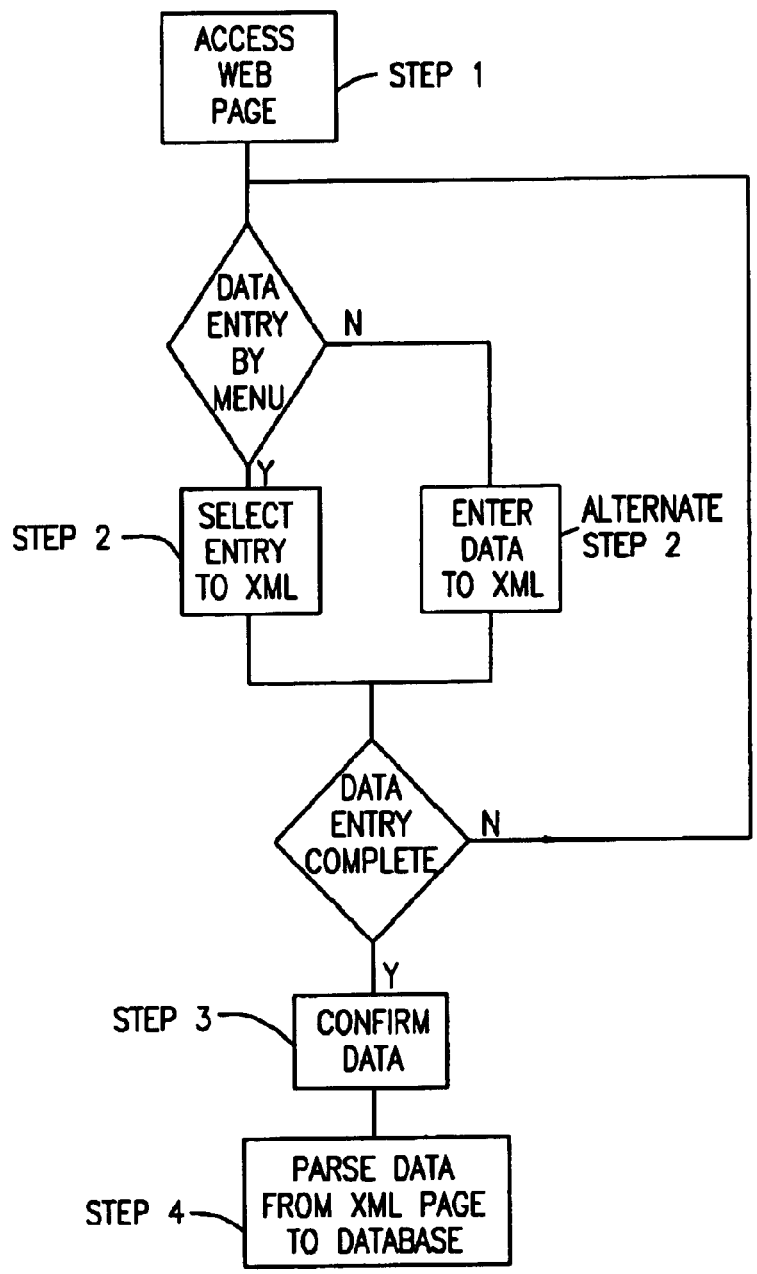
FIG. 18 is a flow chart depicting the data flow steps of the present invention.

The interface software displays the information to the user through the interface of the present invention in the exemplary version described herein. A web page text file incorporating a set of HTML tags describes how the text should be formatted when a browser displays it on the screen. The tags are simple instructions that tell the Web browser how the page should look when it is displayed. A Web browser, like Netscape Navigator™ or Microsoft Internet Explorer™, requests a page, so that the browser can pull the page through the network and into the users machine and interprets the set of HTML tags within the page in order to display the page on the users screen. Additionally, the interface software includes logic, which controls the flow of data to and from the user interface. The interface logic includes a dynamic XML component that reads data entry choices from the database, displays those choices on the interface and records the users selections on a dynamic web page. Once the user has confirmed the selections the dynamic XML component parses the data to a storage database. The process can be described with respect to the FIG. 18. In step 1, the user accesses a web page of the current invention, wherein the dynamic XML component refers to the thesauri database. The XML component reads the appropriate common language term to be displayed in each pull down menu field of the accessed web page. Each common language term is linked to the appropriate medical dictionary term and code in a corresponding thesaurus of the database. In step 2 a user selects a data entry term from the plurality of data terms listed in a particular pull down menu. The dynamic XML component, in response to the selection made by the user, reads the user selection, from the interface and writes that data into a dynamic XML page together with the corresponding term and code from the linked thesauri. The dynamic web page is established by the dynamic XML component for each event report initiated by a user, and is provided to temporarily maintain the data until the user has completed all data entry. In that way any changes or edits can be easily made prior to writing the data to the storage medium of the database. By utilizing the dynamic XML component all logic can be contained in the dynamic XML component, and the database can be a simple storage device. Therefore, any changes with respect to how the data is saved can be implemented in the XML component without the need to change or amend the database. In alternate step 2 the user may provide a response to an information request by manually entering the data in a free form data field. In the exemplary version described here as a web based user interface, the user would position the cursor into a free form data field and type the data entry. The XML component then reads the data entered and writes the response to the dynamic XML page. The XML component also flags certain response for further review by a safety monitor. Those responses include; manually entered responses, and responses which indicate that the reported event may be potentially serious and/or non-labeled. The seriousness of an event is determined by automatically assessment of the selected outcomes vs. a standard list of "serious" outcomes as defined by the regulatory bodies. The "labeled-ness" of the event is automatically determined by comparing the selected symptoms with a pre-defined list of MedDRA or other schema of preferred terms, characterized by the manufacturer as "labeled" or "potentially labeled". In that way an additional quality control check is added for data that is, manually entered by the user that may be prone to errors, inconsistencies and/or inaccuracies. Steps 2 and alternate step 2 are repeated by the user until all data has been entered. The XML component will write each data entry to the dynamic XML page. In step 3 the user is presented with a web page that displays all data entered with respect to the event being reported. The user can then confirm or edit the displayed responses and then enter a final confirmation by clicking a provided button. After the user issues a final confirmation, the XML component will then parse the data, step 4, held on the XML page into the appropriate data fields in the database where the data is permanently stored.

The data is permanently stored using a database server. The database server is an application program that interacts with a database. Generally, the functions of the database server are to receive requests for information directed to the database, format the requests into queries that are understood by the database, submit the requests to the database, receive one or more results from the database, format the results, and deliver the formatted results to one or more other application programs. For example, the database server may receive a request for information in the database in the form of a Structured Query Language (SQL) statement that identifies one or more tables in the database. The database server verifies that the SQL statement has correct syntax and identifies information that is actually in the database. The database server submits the SQL statement to the database and receives a result set of records from one or more database tables.

The browsing engine is an application program that interacts with the other application programs to carry out a method of browsing a hypertext system in the manner described further herein. Generally, the browsing engine establishes one or more connections with one or more clients, presents a view of hypertext documents in the database to the clients, receives information that identifies which documents in the database are relevant to the clients, creates a ranked list of the documents based upon the relevance information, and provides the ranked list to the clients. Other functions of the browsing engine are apparent from the description herein.

V. Embodiments

In an alternate embodiment, the present invention can be utilized to automate the process of collecting data having significance to a particular group of users. For example, the present invention could be used to report problems with consumer goods, such as automobiles. Complaints and problems with new automobiles are monitored by the manufacturer for quality control, by consumer groups to gauge value, and by the federal government for recall purposes. In an alternate embodiment of the present invention, certain aspects would be adapted to the alternate use. For example, the interface and database of the current invention could be adapted for use in receiving reports on automobile defects and problems.

With respect to the user interface, the user would be presented with pages containing images and information consistent with the purpose of the site. For example the network site embodying the present invention could include a consumer path a manufacturer path and a monitor path. The site could provide a means for a consumer to easily and efficiently report problems regarding a vehicle to the manufacturer. In this alternate embodiment, a consumer path would replace the patient path. FIGS. 10a,b,c would alternately depict a diagram of a generic vehicle, which the user would be able to click on to select various systems and sub-systems. As in the current embodiment, selecting a system or sub-system, would display to the user a plurality of pull down menus containing a list of problems associated with that area of the vehicle that the user could click on in order to report a problem or difficulty. It is obvious to one skilled in the art that the system embodying the present invention could be further modified to accommodate this or other alternate embodiments. Other alternate embodiments could include a system for reporting problems with consumer goods other that motor vehicles and health or disease control problems with respect to animals. Other uses and modifications to the present invention will be obvious to those skilled in the art.

The techniques described here are not limited to any particular hardware or software configuration; they may find applicability in any computing or processing environment. For example, functions described as being performed by a server can be distributed across different platforms. Moreover, the techniques may be implemented in hardware or software, or a combination of the two. Preferably, the techniques are implemented in computer programs executing on programmable computers that each include a processor, a storage medium readable by the processor (including volatile and non-volatile memory and/or storage elements), at least one input device and one or more output devices. Program code is applied to data entered using the input device to perform the functions described and to generate output information. The output information is applied to one or more output devices.

Each program is preferably implemented in a high level procedural or object oriented programming language to communicate with a computer system, however, the programs can be implemented in assembly or machine language, if desired. In any case, the language may be a compiled or interpreted language.

Each such computer program is preferably stored-on a storage medium or device (e.g., CD-ROM, hard disk or magnetic diskette) that is readable by a general or special purpose programmable computer for configuring and operating the computer when the storage medium or device is read by the computer to perform the procedures described in this document. The system may also be considered to be implemented as a computer-readable storage medium, configured with a computer program, where the storage medium so configured causes a computer to operate in a specific and predefined manner.

Thus, the foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A computer-based method of facilitating and structuring the intake, investigation, follow-up, analysis and reporting of adverse event and product complaint data; said method comprising:

associating each one of a selectable plurality of familiar popular terms with one or more related standardized terms;

providing a user interface having said selectable plurality of familiar popular terms and a related selectable graphical depiction to enable a user to 1) report adverse events and product complaints data associated with said selectable graphical depiction, 2) review said reported data for accuracy and 3) monitor said reported data; and;

said user using said interface, selecting one or more of said selectable plurality of familiar terms and at least a portion of said selectable graphical depiction to describe an adverse event or product complaint associated with said selected portion of said selectable graphical depiction;

generating a standardized adverse event or product complaint report comprising said one or more related standardized terms associated with said selected one or more of said selectable plurality of familiar popular terms.

2. The method of claim 1 further comprising transmitting said standardized report to an appropriate regulatory body.

3. The method of claim 1 further comprising storing said popular and standardized terms associations in a storage medium.

4. The method of claim 3 further comprising storing said standardized report in a cage medium.

5. The method of claim 4 further comprising associating said selected one or more of said plurality of selectable poplar terms and related standardized term(s) with said selected at least a portion of said selectable graphical depiction and storing said associations in said storage medium.

6. The method of claim 1 further comprising editing said reported adverse event data.

7. The method of claim 1 wherein said plurality of popular terms comprises descriptive medical and diagnostic indicia.

8. The method of claim 1 wherein said plurality of popular terms comprises performance measurement information.

9. The method of claim 1 wherein said graphical depiction comprises an animal body and wherein said plurality of popular terms comprises related common descriptive terms.

10. The method of claim 1 wherein said graphical depiction comprises a human body and wherein said plurality of popular terms comprises related common descriptive terms.

11. The method of claim 1 wherein said graphical depiction comprises a product and wherein said plurality of popular terms comprises related common descriptive terms.

12. The method of claim 1 wherein said graphical depiction comprises a mechanical system and wherein said plurality of popular terms comprises related common descriptive terms.

13. The method of claim 1 wherein said graphical depiction comprises an electrical system and wherein said plurality of popular terms comprises related common descriptive terms.

14. The method of claim 1 wherein said graphical depiction comprises a biological system and wherein said plurality of popular terms comprises related common descriptive terms.

15. The method of claim 1 wherein said graphical depiction comprises a chemical system and wherein said plurality of popular terms comprises related common descriptive terms.

16. The method of claim 1 wherein said graphical depiction comprises a hybrid system and wherein said plurality of popular terms comprises related common descriptive terms.

17. A system for facilitating and structuring the intake, investigation, follow-up, analysis and reporting of adverse event and product complaint data, comprising:

a processor configured to:

associate each one of a plurality of selectable familiar popular terms with one or more related standardized terms;

generate a user interface having said familiar popular terms and a related selectable graphical depiction to enable a user to: 1) report adverse events and product complaints data with said selectable graphical depiction, 2) review said reported data for accuracy and 3) monitoring said reported data;

process said user's selected one or more of said plurality of familiar popular terns and selected at least a portion of said graphical depiction in accordance with a description of an adverse event or product complaint associated with said selected at least a portion of said graphical depiction; and generate a standardized adverse event or product complaint report comprising said one or more related standardized terms associated with said selected familiar popular terms and graphical depiction.

18. The system of claim 17 wherein said processor is in communication with an appropriate regulatory body and is further configured to transmit said standardized report to said appropriate regulatory body.

19. The system of claim 17 further comprising a storage medium and wherein said processor is further configured to store said standardized report in said storage medium.

20. The system of claim 19 wherein said processor is further configured to store said popular and standardized terms associations in said storage medium.

21. The system of claim 20 wherein said processor is further figured to associate said selected one or more of said plurality of selectable popular teems and related standardized term(s) with said selected at least a portion of said selectable graphical depiction and storing said terms-graphical depiction associations in said storage medium.

22. The system of claim 17 wherein said processor is further configured to edit said reported adverse event data.

23. The system of claim 17 wherein said plurality of popular terms comprises medical and diagnostic indicia.

24. The system of claim 17 wherein said plurality of popular terms comprises performance measurement information.

25. The system of claim 17 wherein said graphical depiction comprises an animal body and wherein said plurality of popular terms related common descriptive tams.

26. The system of claim 17 wherein said graphical depiction comprises a human body and wherein said plurality of popular terms comprises related common descriptive terms.

27. The system of claim 17 wherein said graphical depiction comprises a product and wherein said plurality of popular terms comprises related common descriptive terms.

28. The system of claim 17 wherein said graphical depiction comprises a mechanical system and wherein said plurality of popular terms comprises related common descriptive terms.

29. The system of claim 17 wherein said graphical depiction comprises an electrical system and wherein said plurality of popular terms comprises related common descriptive terms.

30. The system of claim 17 wherein said graphical depiction comprises a biological system and wherein said plurality of popular terms comprises related common descriptive terms.

31. The system of claim 17 wherein said graphical depiction comprises a chemical system and wherein said plurality of popular terms comprises related common descriptive terms.

32. The system of claim 17 wherein said graphical depiction comprises a hybrid system and wherein said plurality of popular terms comprises related common descriptive terms.

* * * * *